United States Patent
Yao et al.

(10) Patent No.: US 9,657,280 B2
(45) Date of Patent: *May 23, 2017

(54) BRASSICA AHAS GENES AND GENE ALLELES THAT PROVIDE RESISTANCE TO IMIDAZOLINONE HERBICIDES

(75) Inventors: Kening Yao, Saskatoon (CA); Derek A. Potts, Saskatoon (CA); Bradley D. Leibel, Saskatoon (CA); Daryl R. Males, Saskatoon (CA)

(73) Assignee: Viterra Inc., Regina (CA)

( * ) Notice: Subject to any disclaimer, the term of this patent is extended or adjusted under 35 U.S.C. 154(b) by 1663 days.

This patent is subject to a terminal disclaimer.

(21) Appl. No.: 12/032,199

(22) Filed: Feb. 15, 2008

(65) Prior Publication Data

US 2009/0013424 A1 Jan. 8, 2009

Related U.S. Application Data

(62) Division of application No. 11/079,122, filed on Mar. 14, 2005, now Pat. No. 7,355,098.

(60) Provisional application No. 60/581,315, filed on Jun. 22, 2004.

(51) Int. Cl.
*A01H 5/10* (2006.01)
*C12N 9/10* (2006.01)
*C12N 9/88* (2006.01)
*C12N 15/82* (2006.01)

(52) U.S. Cl.
CPC ............ *C12N 9/1022* (2013.01); *A01H 5/10* (2013.01); *C12N 9/88* (2013.01); *C12N 15/8274* (2013.01)

(58) Field of Classification Search
None
See application file for complete search history.

(56) References Cited

U.S. PATENT DOCUMENTS

| | | | |
|---|---|---|---|
| 4,761,373 A | 8/1988 | Anderson et al. | |
| 5,013,659 A | 5/1991 | Bedbrook et al. | |
| 5,304,732 A | 4/1994 | Anderson et al. | |
| 5,331,107 A | 7/1994 | Anderson et al. | |
| 5,731,180 A | 3/1998 | Dietrich | |
| 5,767,361 A | 6/1998 | Dietrich | |
| 5,853,973 A * | 12/1998 | Kakefuda et al. | 435/4 |
| 5,928,937 A | 7/1999 | Kakefuda et al. | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,225,105 B1 | 5/2001 | Sathasivan et al. | |
| 6,339,184 B1 | 1/2002 | Smith | |
| 6,613,963 B1 * | 9/2003 | Gingera et al. | 800/306 |
| 6,936,751 B2 | 8/2005 | Charne et al. | |
| 7,232,942 B2 | 6/2007 | Slinkard et al. | |
| 7,595,177 B2 * | 9/2009 | Barnes et al. | 435/91.2 |
| 2003/0096277 A1 | 5/2003 | Chen | |
| 2003/0097692 A1 | 5/2003 | Jander et al. | |
| 2004/0142353 A1 | 7/2004 | Cheung et al. | |
| 2004/0237134 A1 | 11/2004 | Pozniak et al. | |
| 2004/0244080 A1 | 12/2004 | Hucl | |
| 2005/0044597 A1 | 2/2005 | Konzak | |
| 2006/0010514 A1 | 1/2006 | Birk | |

FOREIGN PATENT DOCUMENTS

| | | |
|---|---|---|
| EP | 0 360 750 A2 | 3/1990 |
| EP | 0 375 875 | 7/1990 |
| EP | 0 508 161 A1 | 10/1992 |
| EP | 0 525 384 A2 | 2/1993 |
| WO | WO 90/14000 A1 | 11/1990 |
| WO | WO 00/03763 | 9/2000 |
| WO | WO 01/92512 A2 * | 12/2001 |
| WO | WO 02/092820 A1 | 11/2002 |
| WO | WO 03/013225 A2 | 2/2003 |
| WO | WO 03/014356 A2 | 2/2003 |
| WO | WO 03/014357 A1 | 2/2003 |
| WO | WO 2004/016073 | 2/2003 |

OTHER PUBLICATIONS

Rutledge et al 1991, Molecular and General Genetics 229: 31-40.*
Tranel et al 2002 Weed Science 50: 700-712.*
Lee et al, FEBS Letters 1999 452:341-345.*
Zhu et al 2000, Nature Biotechnology 18: 555-558.*
Barrett, M., "Protection of Grass Crops from Sulfonylurea and Imidazolinone Toxicity," *Crop Safeners for Herbicides*, 1989, pp. 195-220, Academic Press, Inc.
Brown, M., et al., "Hydrolytic Activation versus Oxidative Degradation of Assert Herbicide, an Imidazolinone Aryl-carboxylate, in Susceptible Wild Oat versus Tolerant Corn and Wheat," *Pesticide Biochemistry and Physiology*, 1987, pp. 24-29, vol. 27, Academic Press, Inc.
Chang, A., and R. Duggelby, "Herbicide-resistant Forms of *Arabidopsis thaliana* Acetohydroxyacid Synthase: Characterization of the Catalytic Properties and Sensitivity to Inhibitors of Four Defined Mutants," *Biochemistry J.*, 1998, pp. 765-777, vol. 333.
Chong C., and J. Choi, "Amino Acid Residues Conferring Herbicide Tolerance in Tobacco Acetolactate Synthase," *Biochemical and Biophysical Research Communications*, 2000, pp. 462-467, vol. 279, Academic Press.
Hattori, J., et al., "Multiple Resistance to Sulfonylureas and Imidazolinones Conferred by an Acetohydroxyacid Synthase Gene with Separate Mutations for Selective Resistance," *Molecular Genetics*, 1992, pp. 167-173, vol. 232.

(Continued)

*Primary Examiner* — David H Kruse
(74) *Attorney, Agent, or Firm* — Mintz, Levin, Cohn, Ferris, Glovsky and Popeo P.C.

(57) ABSTRACT

Plants, plant parts and plant seeds that are resistant to imidazolinone herbicides are provided. Plants are disclosed that contain a mutation in an AHAS gene. Specifically, plants are disclosed that contain a mutant AHAS gene allele of the *Brassica juncea* B genome. Two *B. juncea* AHAS gene sequences (BjAHAS-a and BjAHAS-b) and one *B. nigra* AHAS gene sequence (BngrAHAS) are disclosed. The sequence of the mutant allele, BjAHAS-bR, is also disclosed. Various methods are disclosed that include creation of mutant *B. juncea* lines, selection for herbicide resistant lines and determining the presence of the BjAHAS-bR mutant allele after crosses.

18 Claims, 2 Drawing Sheets

(56) References Cited

OTHER PUBLICATIONS

Mourad, G., et al., "Isolation and Genetic Analysis of a Triazolopyrimidine-Resistant Mutant of *Arabidopsis*," *J. Heredity*, 1993, pp. 91-96, vol. 84.

Newhouse, K., et al., "Mutations in corn (*Zea mays* L.) Conferring Resistance to Imidazolinone Herbicides," *Theor. Appl. Genet.*, 1991, pp. 65-70, vol. 83, Springer-Verlag.

Newhouse, K., et al., "Tolerance to Imidazolinone Herbicides in Wheat," *Plant Physiology*, 1992, pp. 882-886, vol. 100.

Odell, et al., "Comparison of Increased Expression of Wild-Type and Herbicide-Resistant Acetolactate Synthase Genes in Transgenic Plants, and Indication of Posttranscriptional Limitation on Enzyme Activity," *Plant Physiol.*, (1990), pp. 1647-1654, vol. 94.

Ott, K., et al., "Rational Molecular Design and Genetic Engineering of Herbicide Resistant Crops by Structure Modeling and Site-directed Mutagenesis of Acetohydroxyacid Synthase," *J. Mol. Biol.*, 1996, pp. 359-368, vol. 263, Academic Press Limited.

Repellin, A., et al., "Genetic Enrichment of Cereal Crops via Alien Gene Transfer: New Challenges," *Plant Cell, Tissue and Organ Culture*, 2001, pp. 159-183, vol. 64.

Sathasivan, K., et al., "Nucleotide Sequence of a Mutant Acetolactate synthase Gene from an Imidaziolinone-resistant *Arabidopsis thaliana* var. Columbia," *Nucleic Acids Research*, 1990, pp. 2188, vol. 18(8), Oxford University Press.

Sathasivan, K., et al., "Molecular Basis of Imidazolinone Herbicide Resistance in *Arabidopsis thaliana* var Columbia," *Plant Physiol.*, 1991, pp. 1044-1050, vol. 97.

Sebastian, S., et al., "Semidominant Soybean Mutation for Resistance to Sulfonylurea9erbicides," *Crop. Sci.*, 1989, pp. 1403-1408, vol. 29.

Shaner, D. et al., "Imidazolinone-Resistant Crops: Selection, Characterization, and Management," *Herbicide-Resistant Crops: Agricultural, Environmental, Economic*, 1996, pp. 143-157.

Shaner, D. and P.A. Robson, "Absorption, Translocation, and Metabolism of AC 252 214 in Soybean (*Glycine max*), Common Cocklebur (*Xanthium strumarium*), and Velvetleaf (*Abutilon theophrasti*)," *Weed Sci.*, 1985, pp. 469-471, vol. 33.

Shaner, D., et al., "Imidazolinones: Potent Inhibitors of Acetohydroxyacid Synthase," *Plant Physiol.*, 1984, pp. 545-546, vol. 76.

Singh, B.K., "Biosynthesis of Valine, Leucine and Isoleucine," *Plant Amino Acids*, 1999, pp. 227-247, Marcel Dekker Inc., New York, NY.

Swanson, E., et al., "Microspore Mutagenesis and Selection: Canola Plants with Field Tolerance to the Imidazolinones," *Theor. Appl. Genet.*, 1989, pp. 525-530, vol. 78, Springer-Verlag.

Wright, T.R. and D. Penner, "Cell Selection and Inheritance of Imidazolinone Resistance in Sugarbeet (*Beta vulgaris*)," *Theor. Appl. Genet.*, 1998, pp. 612-620, vol. 96, Springer-Verlag.

GenBank Accession No. BE417248, Jul. 24, 2000.

GenBank Accession No. BF200418, Nov. 6, 2000.

EMBL Accession No. AF059600, Apr. 27, 1998.

Duggleby, R., at al., "Systematic Characterization of Mutations in Yeast Acetohydroxyacid Synthase," *Eur. J. Biochem.*, 2003, pp. 2895-2904, vol. 270.

Lee, Y., et al., "Effect of Mutagenesis at Serine 653 of *Arabidopsis thaliana* Acetohydroxyacid Synthase on the Sensitivity to Imidazolinone and Sulfonylurea Herbicides," *FEBS Letters*, 1999, pp. 341-45, vol. 452, Federation of European Biochemical Societies.

EMBL: AY210405, Mar. 12, 2003.

EMBL: AY210407, Mar. 12, 2003.

Hattori, J., et al., "An Acetohydroxyacid Synthase Mutant Reveals a Single Site Involved in Multiple Herbicide Resistance," *Molecular and General Genetics*, 1995, pp. 419-425, vol. 246, Springer Verlag, Berlin, Germany.

Pozniak, C.J., et al., "Physiological and Molecular Characterization of Mutation-Derived Imidazolinone Resistance in Spring Wheat," 2004, *Crop Science*, pp. 1434-1443, vol. 44(4).

Ascenzi, R., et al., (2003) International Society of Plant Molecular Biologists Congress, Barcelona, Spain, Ref. No. S10-17.

Siwach., et al., "Molecular Biology (Principles and Practices)," University Science Press, 2009, pp. 274-275.

Commission on Genetic Modification (COGEM), "The status of oligonucleotides within the context of site-directed mutagenesis," COGEM advice and report CGM/100701-03, Jul. 1, 2010.

\* cited by examiner

FIGURE 2

| | | | | | | |
|---|---|---|---|---|---|---|
| *BjAHAS-b* | ATC | CCA | AGT | GGT | GGT | SEQ ID NO:16 |
| | I | P | S | G | G | SEQ ID NO:20 |
| *BjAHAS-bR* | ATC | CCA | AAT | GGT | GGT | SEQ ID NO:17 |
| | I | P | N | G | G | SEQ ID NO:21 |
| *AtAHAS* | ATC | CCG | AGT | GGT | GGC | SEQ ID NO:18 |
| | I | P | S | G | G | SEQ ID NO:22 |
| *Imr1* | ATC | CCG | AAT | GGT | GGC | SEQ ID NO:19 |
| | I | P | N | G | G | SEQ ID NO:23 | ial is a divisional of U.S. application Ser.

SEQUENCE LISTING

<160> NUMBER OF SEQ ID NOS: 25

<210> SEQ ID NO 1
<211> LENGTH: 24

```
<212> TYPE: DNA
<213> ORGANISM: Artificial Sequence
<220> FEATURE:
<223> OTHER INFORMATION: Primer
<221> NAME/KEY: misc_feature
<222> LOCATION: (3)...(3)
<223> OTHER INFORMATION: n is a, c, g, or t
<221> NAME/KEY: misc_feature
<222> LOCATION: (6)...(6)
<223> OTHER INFORMATION: n is a, c, g, or t
<221> NAME/KEY: misc_feature
<222> LOCATION: (9)...(9)
<223> OTHER INFORMATION: n is a, c, g, or t

<400> SEQUENCE: 1
ggngcntcna tggarathca ycar                                          24

<210> SEQ ID NO 2
<211> LENGTH: 24
<212> TYPE: DNA
<213> ORGANISM: Artificial Sequence
<220> FEATURE:
<223> OTHER INFORMATION: Primer
<221> NAME/KEY: misc_feature
<222> LOCATION: (7)...(7)
<223> OTHER INFORMATION: n is a, c, g, or t
<221> NAME/KEY: misc_feature
<222> LOCATION: (10)...(10)
<223> OTHER INFORMATION: n is a, c, g, or t
<221> NAME/KEY: misc_feature
<222> LOCATION: (13)...(13)
<223> OTHER INFORMATION: n is a, c, g, or t
<221> NAME/KEY: misc_feature
<222> LOCATION: (19)...(19)
<223> OTHER INFORMATION: n is a, c, g, or t

<400> SEQUENCE: 2
rtayttngtn cgnccrtcnc cytc                                          24

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
tggtggaagc ttgaactcg                                                19

<210> SEQ ID NO 4
<211> LENGTH: 37
<212> TYPE: DNA
<213> ORGANISM: Artificial Sequence
<220> FEATURE:
<223> OTHER INFORMATION: Primer

<400> SEQUENCE: 4
gtaaaacgac ggccagtcga tttttttttt ttttttt                            37

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtaaaacgac ggccagtcga                                               20
```

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cacgttcaca aactcattca tca                                              23

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
actcgagttc aagcttccac ca                                               22

<210> SEQ ID NO 8
<211> LENGTH: 2015
<212> TYPE: DNA
<213> ORGANISM: Brassica juncea

<400> SEQUENCE: 8

```
cacgttcaca aactcattca tcatctctct ctcatttctc tctctctcat ctaaccatgg      60
cggcggcaac atcgtcttct ccgatctcct taaccgctaa accttcttcc aaatcccctc     120
tacccatttc cagattctcc cttcccttct ccttaacccc acagaaaccc tcctcccgtc     180
tccaccgtcc tctcgccatc tccgccgttc tcaactcacc cgtcaatgtc gcacctgaaa     240
aaaccgacaa gatcaagact ttcatctccc gctacgctcc cgacgagccc cgcaagggtg     300
ctgatatcct cgtggaagcc ctcgagcgtc aaggcgtcga aaccgtcttc gcttatcccg     360
gaggtgcctc catggagatc caccaagcct tgactcgctc ctccaccatc cgtaacgtcc     420
tcccccgtca cgaacaagga ggagtcttcg ccgccgaggg ttacgctcgt tcctccggca     480
aaccgggaat ctgcattgcc acttcgggtc ccggagctac caacctcgtc agcgggttag     540
ccgacgcgat gcttgacagt gttcctctcg tgccattac aggacaggtc cctcgccgga     600
tgatcggtac tgacgccttc caagagacgc caatcgttga ggtaacgagg tctattacga     660
aacataacta tctggtgatg gatgttgatg acatacctag gatcgttcaa gaagcttttc     720
ttctagctac ttccggtaga cccggaccgg ttttggttga cgttcctaag gatattcagc     780
agcagcttgc gattcctaac tgggatcaac ctatgcgctt gcctggctac atgtctaggc     840
tgcctcagcc accggaagtt tctcagttag gtcagatcgt taggttgatc tcggagtcta     900
agaggcctgt tttgtacgtt ggtggtggaa gcttgaactc gagtgaagaa ctggggagat     960 tgtcgagct tactgggatc cctgttgcga gtacgttgat ggggcttggc tcttatcctt    1020
gtaacgatga gttgtccctg cagatgcttg gcatgcacgg gactgtgtat gctaactacg    1080
ctgtggagca tagtgatttg ttgctggcgt ttggtgttag gtttgatgac cgtgtcacgg    1140
gaaagctcga ggcgttttgcg agcagggcta agattgtgca catagacatt gattctgctg    1200
agattgggaa gaataagaca cctcacgtgt ctgtgtgtgg tgatgtaaag ctggctttgc    1260
aagggatgaa caaggttctt gagaaccggg cggaggagct caagcttgat ttcggtgttt    1320
ggaggagtga gttgagcgag cagaaacaga agttcccgtt gagcttcaaa acgtttggag    1380
aagccattcc tccgcagtac gcgattcagg tcctagacga gctaaccaa gggaaggcaa    1440
```

-continued

| | |
|---|---|
| ttatcagtac tggtgttgga cagcatcaga tgtgggcggc gcagttttac aagtacagga | 1500 |
| agccgaggca gtggctgtcg tcctcaggac tcggagctat gggtttcgga cttcctgctg | 1560 |
| cgattggagc gtctgtggcg aaccctgatg cgattgttgt ggacattgac ggtgatggaa | 1620 |
| gcttcataat gaacgttcaa gagctggcca caatccgtgt agagaatctt cctgtgaaga | 1680 |
| tactcttgtt aaacaaccag catcttggga tggtcatgca atgggaagat cggttctaca | 1740 |
| aagctaacag agctcacact tatctcgggg acccggcaag ggagaacgag atcttcccta | 1800 |
| acatgctgca gtttgcagga gcttgcggga ttccagctgc gagagtgacg aagaaagaag | 1860 |
| aactccgaga agctattcag acaatgctgg atacacctgg accgtacctg ttggatgtca | 1920 |
| tctgtccgca ccaagaacat gtgttaccga tgatcccaag tggtggcact ttcaaagatg | 1980 |
| taataaccga aggggatggt cgcactaagt actga | 2015 |

<210> SEQ ID NO 9
<211> LENGTH: 2024
<212> TYPE: DNA
<213> ORGANISM: Brassica juncea

<400> SEQUENCE: 9

| | |
|---|---|
| cacgttcaca aactcattca tcatctctcg ctcatttctc tccctctcct ctaaccatgg | 60 |
| cggcggcaac atcgtcttct ccaatctcct tcaccgctaa accttcttcc aaatcccttt | 120 |
| tacccatttc cagattctcc cttcccttct ccttaatccc gcagaaaccc tcctcccttc | 180 |
| gccacagtcc tctctccatc tcagccgttc tcaacacacc cgtcaatgtc gcacctcctt | 240 |
| cccctgaaaa aattgaaaag aacaagactt tcatctcccg ctacgctccc gacgagcccc | 300 |
| gcaagggcgc cgatatcctc gtcgaagccc tcgagcgtca aggcgtcgaa accgtcttcg | 360 |
| cttacccggg aggtgcttcc atggagatcc accaagcctt aactcgatcc tctaccatcc | 420 |
| gtaacgtcct cccccgtcac gaacaaggag gagtctttgc cgccgagggt tacgctcgtt | 480 |
| cctctggtaa accgggaatc tgcatagcca cgtcaggtcc cggagccacc aacctcgtta | 540 |
| gcggtttagc cgacgcgatg ctcgacagtg tccctctcgt cgctattaca ggacaggtcc | 600 |
| ctcgtcggat gattggtact gacgcgttcc aggagacgcc aatcgttgag gtaacgaggt | 660 |
| ctattacgaa acataactat ctggtcatgg atgttgatga catacctagg atcgtgcaag | 720 |
| aggctttctt tctagctact tccggtagac ccggaccggt tttagttgat gttcctaagg | 780 |
| atattcagca gcagcttgcg attcctaact gggatcagcc tatgcgctta cctggttaca | 840 |
| tgtctaggct gcctcagcct ccggaagttt ctcagttagg gcagatcgtt aggttgatct | 900 |
| ctgaatctaa gaggcctgtt tgtatgttg gtggtggaag cttgaactcg agtgatgaac | 960 |
| tggggaggtt tgtggagctt actgggatcc ctgtcgcgag tactttgatg gggcttggtt | 1020 |
| cttatccttg taacgatgag ttgtctctgc agatgcttgg tatgcacggg actgtgtacg | 1080 |
| ctaattacgc tgtggagcat agtgatttgt tgctggcgtt tggtgttagg tttgatgacc | 1140 |
| gtgtcactgg aaagctcgag gcttttgcga gcagggctaa gattgtgcac attgacattg | 1200 |
| attctgctga gattgggaag aacaagacgc ctcatgtgtc tgtgtgtggt gatgttaagc | 1260 |
| tggctttgca agggatgaac aaggttcttg agaaccgagc agaggagctc aagcttgact | 1320 |
| tcggagtttg gaggagtgaa ttgagcgagc agaaacaaaa gttcccgttg agttttaaaa | 1380 |
| cgtttggaga agctattcct ccacagtacg cgattcaggt cctcgacgag ctaaccgatg | 1440 |
| ggaaggcaat catcagtact ggtgttggc aacatcagat gtgggcgcg cagttttaca | 1500 |
| agtacaggaa gccgaggcag tggttgtcat catcaggcct tggagctatg ggttttggac | 1560 |

```
ttcctgctgc cattggagcg tctgtggcga accctgatgc gattgttgtg gacattgacg    1620
gtgacggaag cttcatcatg aatgttcaag agctggccac aatccgtgta gagaatcttc    1680
ctgtgaaggt actcttgtta aacaaccagc atcttggcat ggttatgcaa tgggaagatc    1740
ggttctacaa agctaacaga gctcacactt atctcgggga tccggcaaag gagaacgaga    1800
tcttcccaaa catgctgcag tttgcaggag cctgtgggat tccagctgcg agggtgacga    1860
agaaagaaga actccgagat gctattcaga caatgctgga tacaccagga ccatacctgt    1920
tggatgtgat ctgtccgcac aagagcatg tgttaccgat gatcccaagt ggtggtactt    1980
tcaaagatgt cataacagaa ggggatggtc gcactaagta ctga                    2024

<210> SEQ ID NO 10
<211> LENGTH: 2024
<212> TYPE: DNA
<213> ORGANISM: Brassica nigra

<400> SEQUENCE: 10
cacgttcaca aactcattca tcatctctcg ctcatttctc tccctctcct ctaaccatgg      60
cggcggcaac atcgtcttct ccaatctcct tcaccgctaa accttcttcc aaatcccttt     120
tacccatttc cagattctcc cttcccttct ccttaatccc gcagaaaccc tcctcccttc     180
gccacagtcc tctctccatc tcagccgttc tcaacacacc cgtcaatgtc gcacctcctt     240
cccctgaaaa aattgaaaag aacaagactt tcatctcccg ctacgctccc gacgagcccc     300
gcaagggcgc cgatatcctc gtcgaagccc tcgagcgtca aggcgtcgaa accgtcttcg     360
cttacccggg aggtgcttcc atggagatcc accaagcctt aactcgatcc tctaccatcc     420
gtaacgtcct cccccgtcac gaacaaggag gagtctttgc cgccgagggt tacgctcgtt     480
cctctggtaa accgggaatc tgcatagcca cgtcaggtcc cggagccacc aacctcgtta     540
gcggtttagc cgacgcgatg ctcgacagtg tccctctcgt cgctattaca ggacaggtcc     600
ctcgtcggat gattggtact gacgcgttcc aggagacacc aatcgttgag gtaacgaggt     660
ctattacgaa acataactat ctggtcatgg atgttgatga catacctagg atcgtgcaag     720
aggctttctt tctagctact tccggtagac ccggaccggt tttagttgat gttcctaagg     780
atattcagca gcagcttgcg attcctaact gggatcagcc tatgcgctta cctggttaca     840
tgtctaggct gcctcagcct ccggaagttt ctcagttagg gcagatcgtt aggttgatct     900
ctgaatctaa gaggcctgtt ttgtatgttg gtggtggaag cttgaactcg agtgatgaac     960
tggggaggtt tgtggagctt actgggatcc ctgtcgcgag tactttgatg gggcttggtt    1020
cttatccttg taacgatgag ttgtctctgc agatgcttgg tatgcacggg actgtgtacg    1080
ctaattacgc tgtggagcat agtgatttgt tgctggcgtt tggtgttagg tttgatgacc    1140
gtgtcactgg aaagctcgag gcttttgcga gcagggctaa gattgtgcac attgacattg    1200
attctgctga gattgggaag aacaagacgc ctcatgtgtc tgtgtgtggt gatgttaagc    1260
tggctttgca agggatgaac aaggttcttg agaaccgagc agaggagctc aagcttgact    1320
tcggagtttg gaggagtgaa ttgagcgagc agaaacaaaa gttcccgttg agttttaaaa    1380
cgtttggaga agccattcct ccacagtacg cgattcaggt cctcgacgag ctaaccgatg    1440
ggaaggcaat catcagtact ggtgttgggc aacatcagat gtgggcggcg cagttttaca    1500
agtacaggaa gccgaggcag tggttgtcat catcaggcct tggagctatg gttttggac    1560 ttcctgctgc cattggagcg tctgtggcga accctgatgc gattgttgtg gacattgacg    1620
```

-continued

```
gtgacggaag cttcatcatg aatgttcaag agctggccac aatccgtgta gagaatcttc    1680
ctgtgaaggt actcttgtta acaaccagc atcttggcat ggttatgcaa tgggaagatc    1740
ggttctacaa agctaacaga gctcacactt atctcgggga tccggcaaag gagaacgaga    1800
tcttcccaaa catgctgcag tttgcaggag cctgtgggat tccagctgcg agggtgacga    1860
agaaagaaga actccgagat gctattcaga caatgctgga tacaccagga ccatacctgt    1920
tggatgtgat ctgtccgcac caagagcatg tgttaccgat gatcccaagt ggtggtactt    1980
tcaaagatgt cataacagaa ggggatggtc gcactaagta ctga                     2024
```

<210> SEQ ID NO 11
<211> LENGTH: 652
<212> TYPE: PRT
<213> ORGANISM: Brassica juncea

<400> SEQUENCE: 11

```
Met Ala Ala Ala Thr Ser Ser Pro Ile Ser Leu Thr Ala Lys Pro
  1               5                  10                  15

Ser Ser Lys Ser Pro Leu Pro Ile Ser Arg Phe Ser Leu Pro Phe Ser
                 20                  25                  30

Leu Thr Pro Gln Lys Pro Ser Ser Arg Leu His Arg Pro Leu Ala Ile
             35                  40                  45

Ser Ala Val Leu Asn Ser Pro Val Asn Val Ala Pro Glu Lys Thr Asp
         50                  55                  60

Lys Ile Lys Thr Phe Ile Ser Arg Tyr Ala Pro Asp Glu Pro Arg Lys
 65                  70                  75                  80

Gly Ala Asp Ile Leu Val Glu Ala Leu Glu Arg Gln Gly Val Glu Thr
                 85                  90                  95

Val Phe Ala Tyr Pro Gly Gly Ala Ser Met Glu Ile His Gln Ala Leu
            100                 105                 110

Thr Arg Ser Ser Thr Ile Arg Asn Val Leu Pro Arg His Glu Gln Gly
        115                 120                 125

Gly Val Phe Ala Ala Glu Gly Tyr Ala Arg Ser Ser Gly Lys Pro Gly
    130                 135                 140

Ile Cys Ile Ala Thr Ser Gly Pro Gly Ala Thr Asn Leu Val Ser Gly
145                 150                 155                 160

Leu Ala Asp Ala Met Leu Asp Ser Val Pro Leu Val Ala Ile Thr Gly
                165                 170                 175

Gln Val Pro Arg Arg Met Ile Gly Thr Asp Ala Phe Gln Glu Thr Pro
            180                 185                 190

Ile Val Glu Val Thr Arg Ser Ile Thr Lys His Asn Tyr Leu Val Met
        195                 200                 205

Asp Val Asp Asp Ile Pro Arg Ile Val Gln Glu Ala Phe Phe Leu Ala
    210                 215                 220

Thr Ser Gly Arg Pro Gly Pro Val Leu Val Asp Val Pro Lys Asp Ile
225                 230                 235                 240

Gln Gln Gln Leu Ala Ile Pro Asn Trp Asp Gln Pro Met Arg Leu Pro
                245                 250                 255

Gly Tyr Met Ser Arg Leu Pro Gln Pro Pro Glu Val Ser Gln Leu Gly
            260                 265                 270

Gln Ile Val Arg Leu Ile Ser Glu Ser Lys Arg Pro Val Leu Tyr Val
        275                 280                 285

Gly Gly Gly Ser Leu Asn Ser Ser Glu Glu Leu Gly Arg Phe Val Glu
    290                 295                 300
```

```
Leu Thr Gly Ile Pro Val Ala Ser Thr Leu Met Gly Leu Gly Ser Tyr
305                 310                 315                 320

Pro Cys Asn Asp Glu Leu Ser Leu Gln Met Leu Gly Met His Gly Thr
                325                 330                 335

Val Tyr Ala Asn Tyr Ala Val Glu His Ser Asp Leu Leu Leu Ala Phe
            340                 345                 350

Gly Val Arg Phe Asp Asp Arg Val Thr Gly Lys Leu Glu Ala Phe Ala
        355                 360                 365

Ser Arg Ala Lys Ile Val His Ile Asp Ile Asp Ser Ala Glu Ile Gly
370                 375                 380

Lys Asn Lys Thr Pro His Val Ser Val Cys Gly Asp Val Lys Leu Ala
385                 390                 395                 400

Leu Gln Gly Met Asn Lys Val Leu Glu Asn Arg Ala Glu Glu Leu Lys
                405                 410                 415

Leu Asp Phe Gly Val Trp Arg Ser Glu Leu Ser Glu Gln Lys Gln Lys
            420                 425                 430

Phe Pro Leu Ser Phe Lys Thr Phe Gly Glu Ala Ile Pro Pro Gln Tyr
        435                 440                 445

Ala Ile Gln Val Leu Asp Glu Leu Thr Gln Gly Lys Ala Ile Ile Ser
450                 455                 460

Thr Gly Val Gly Gln His Gln Met Trp Ala Ala Gln Phe Tyr Lys Tyr
465                 470                 475                 480

Arg Lys Pro Arg Gln Trp Leu Ser Ser Gly Leu Gly Ala Met Gly
                485                 490                 495

Phe Gly Leu Pro Ala Ala Ile Gly Ala Ser Val Ala Asn Pro Asp Ala
            500                 505                 510

Ile Val Val Asp Ile Asp Gly Asp Gly Ser Phe Ile Met Asn Val Gln
        515                 520                 525

Glu Leu Ala Thr Ile Arg Val Glu Asn Leu Pro Val Lys Ile Leu Leu
530                 535                 540

Leu Asn Asn Gln His Leu Gly Met Val Met Gln Trp Glu Asp Arg Phe
545                 550                 555                 560

Tyr Lys Ala Asn Arg Ala His Thr Tyr Leu Gly Asp Pro Ala Arg Glu
                565                 570                 575

Asn Glu Ile Phe Pro Asn Met Leu Gln Phe Ala Gly Ala Cys Gly Ile
            580                 585                 590

Pro Ala Ala Arg Val Thr Lys Lys Glu Glu Leu Arg Glu Ala Ile Gln
        595                 600                 605

Thr Met Leu Asp Thr Pro Gly Pro Tyr Leu Leu Asp Val Ile Cys Pro
610                 615                 620

His Gln Glu His Val Leu Pro Met Ile Pro Ser Gly Gly Thr Phe Lys
625                 630                 635                 640

Asp Val Ile Thr Glu Gly Asp Gly Arg Thr Lys Tyr
                645                 650

<210> SEQ ID NO 12
<211> LENGTH: 655
<212> TYPE: PRT
<213> ORGANISM: Brassica juncea

<400> SEQUENCE: 12

Met Ala Ala Ala Thr Ser Ser Ser Pro Ile Ser Phe Thr Ala Lys Pro
1               5                   10                  15

Ser Ser Lys Ser Leu Leu Pro Ile Ser Arg Phe Ser Leu Pro Phe Ser
            20                  25                  30
```

```
Leu Ile Pro Gln Lys Pro Ser Ser Leu Arg His Ser Pro Leu Ser Ile
            35                  40                  45

Ser Ala Val Leu Asn Thr Pro Val Asn Val Ala Pro Pro Ser Pro Glu
 50                  55                  60

Lys Ile Glu Lys Asn Lys Thr Phe Ile Ser Arg Tyr Ala Pro Asp Glu
 65                  70                  75                  80

Pro Arg Lys Gly Ala Asp Ile Leu Val Glu Ala Leu Glu Arg Gln Gly
                 85                  90                  95

Val Glu Thr Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
            115                 120                 125

Glu Gln Gly Gly Val Phe Ala Ala Glu Gly Tyr Ala Arg Ser Ser Gly
        130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Met Asp Val Asp Asp Ile Pro Arg Ile Val Gln Glu Ala Phe
    210                 215                 220

Phe Leu Ala Thr Ser Gly Arg Pro Gly Pro Val Leu Val Asp Val Pro
225                 230                 235                 240

Lys Asp Ile Gln Gln Gln Leu Ala Ile Pro Asn Trp Asp Gln Pro Met
                245                 250                 255

Arg Leu Pro Gly Tyr Met Ser Arg Leu Pro Gln Pro Pro Glu Val Ser
            260                 265                 270

Gln Leu Gly Gln Ile Val Arg Leu Ile Ser Glu Ser Lys Arg Pro Val
        275                 280                 285

Leu Tyr Val Gly Gly Gly Ser Leu Asn Ser Ser Asp Glu Leu Gly Arg
    290                 295                 300

Phe Val Glu Leu Thr Gly Ile Pro Val Ala Ser Thr Leu Met Gly Leu
305                 310                 315                 320

Gly Ser Tyr Pro Cys Asn Asp Glu Leu Ser Leu Gln Met Leu Gly Met
                325                 330                 335

His Gly Thr Val Tyr Ala Asn Tyr Ala Val Glu His Ser Asp Leu Leu
            340                 345                 350

Leu Ala Phe Gly Val Arg Phe Asp Asp Arg Val Thr Gly Lys Leu Glu
        355                 360                 365

Ala Phe Ala Ser Arg Ala Lys Ile Val His Ile Asp Ile Asp Ser Ala
    370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
                405                 410                 415

Glu Leu Lys Leu Asp Phe Gly Val Trp Arg Ser Glu Leu Ser Glu Gln
            420                 425                 430

Lys Gln Lys Phe Pro Leu Ser Phe Lys Thr Phe Gly Glu Ala Ile Pro
        435                 440                 445
```

```
Pro Gln Tyr Ala Ile Gln Val Leu Asp Glu Leu Thr Asp Gly Lys Ala
    450                 455                 460
Ile Ile Ser Thr Gly Val Gly Gln His Gln Met Trp Ala Ala Gln Phe
465                 470                 475                 480
Tyr Lys Tyr Arg Lys Pro Arg Gln Trp Leu Ser Ser Ser Gly Leu Gly
                485                 490                 495
Ala Met Gly Phe Gly Leu Pro Ala Ala Ile Gly Ala Ser Val Ala Asn
            500                 505                 510
Pro Asp Ala Ile Val Asp Ile Asp Gly Asp Gly Ser Phe Ile Met
            515                 520                 525
Asn Val Gln Glu Leu Ala Thr Ile Arg Val Glu Asn Leu Pro Val Lys
    530                 535                 540
Val Leu Leu Leu Asn Asn Gln His Leu Gly Met Val Met Gln Trp Glu
545                 550                 555                 560
Asp Arg Phe Tyr Lys Ala Asn Arg Ala His Thr Tyr Leu Gly Asp Pro
                565                 570                 575
Ala Lys Glu Asn Glu Ile Phe Pro Asn Met Leu Gln Phe Ala Gly Ala
            580                 585                 590
Cys Gly Ile Pro Ala Ala Arg Val Thr Lys Lys Glu Glu Leu Arg Asp
            595                 600                 605
Ala Ile Gln Thr Met Leu Asp Thr Pro Gly Pro Tyr Leu Leu Asp Val
    610                 615                 620
Ile Cys Pro His Gln Glu His Val Leu Pro Met Ile Pro Ser Gly Gly
625                 630                 635                 640
Thr Phe Lys Asp Val Ile Thr Glu Gly Asp Gly Arg Thr Lys Tyr
                645                 650                 655

<210> SEQ ID NO 13
<211> LENGTH: 655
<212> TYPE: PRT
<213> ORGANISM: Brassica nigra

<400> SEQUENCE: 13

Met Ala Ala Ala Thr Ser Ser Ser Pro Ile Ser Phe Thr Ala Lys Pro
  1               5                  10                  15
Ser Ser Lys Ser Leu Leu Pro Ile Ser Arg Phe Ser Leu Pro Phe Ser
                20                  25                  30
Leu Ile Pro Gln Lys Pro Ser Ser Leu Arg His Ser Pro Leu Ser Ile
            35                  40                  45
Ser Ala Val Leu Asn Thr Pro Val Asn Val Ala Pro Pro Ser Pro Glu
    50                  55                  60
Lys Ile Glu Lys Asn Lys Thr Phe Ile Ser Arg Tyr Ala Pro Asp Glu
65                  70                  75                  80
Pro Arg Lys Gly Ala Asp Ile Leu Val Glu Ala Leu Glu Arg Gln Gly
                85                  90                  95
Val Glu Thr Val Phe Ala Tyr Pro Gly Gly Ala Ser Met Glu Ile His
            100                 105                 110
Gln Ala Leu Thr Arg Ser Ser Thr Ile Arg Asn Val Leu Pro Arg His
        115                 120                 125
Glu Gln Gly Gly Val Phe Ala Ala Glu Gly Tyr Ala Arg Ser Ser Gly
    130                 135                 140
Lys Pro Gly Ile Cys Ile Ala Thr Ser Gly Pro Gly Ala Thr Asn Leu
145                 150                 155                 160
Val Ser Gly Leu Ala Asp Ala Met Leu Asp Ser Val Pro Leu Val Ala
                165                 170                 175
```

-continued

```
Ile Thr Gly Gln Val Pro Arg Arg Met Ile Gly Thr Asp Ala Phe Gln
            180                 185                 190
Glu Thr Pro Ile Val Glu Val Thr Arg Ser Ile Thr Lys His Asn Tyr
        195                 200                 205
Leu Val Met Asp Val Asp Ile Pro Arg Ile Val Gln Glu Ala Phe
210                 215                 220
Phe Leu Ala Thr Ser Gly Arg Pro Gly Pro Val Leu Asp Val Pro
225                 230                 235                 240
Lys Asp Ile Gln Gln Gln Leu Ala Ile Pro Asn Trp Asp Gln Pro Met
                245                 250                 255
Arg Leu Pro Gly Tyr Met Ser Arg Leu Pro Gln Pro Pro Glu Val Ser
            260                 265                 270
Gln Leu Gly Gln Ile Val Arg Leu Ile Ser Glu Ser Lys Arg Pro Val
        275                 280                 285
Leu Tyr Val Gly Gly Gly Ser Leu Asn Ser Ser Asp Glu Leu Gly Arg
    290                 295                 300
Phe Val Glu Leu Thr Gly Ile Pro Val Ala Ser Thr Leu Met Gly Leu
305                 310                 315                 320
Gly Ser Tyr Pro Cys Asn Asp Glu Leu Ser Leu Gln Met Leu Gly Met
                325                 330                 335
His Gly Thr Val Tyr Ala Asn Tyr Ala Val Glu His Ser Asp Leu Leu
            340                 345                 350
Leu Ala Phe Gly Val Arg Phe Asp Asp Arg Val Thr Gly Lys Leu Glu
        355                 360                 365
Ala Phe Ala Ser Arg Ala Lys Ile Val His Ile Asp Ile Asp Ser Ala
    370                 375                 380
Glu Ile Gly Lys Asn Lys Thr Pro His Val Ser Val Cys Gly Asp Val
385                 390                 395                 400
Lys Leu Ala Leu Gln Gly Met Asn Lys Val Leu Glu Asn Arg Ala Glu
                405                 410                 415
Glu Leu Lys Leu Asp Phe Gly Val Trp Arg Ser Glu Leu Ser Glu Gln
            420                 425                 430
Lys Gln Lys Phe Pro Leu Ser Phe Lys Thr Phe Gly Glu Ala Ile Pro
        435                 440                 445
Pro Gln Tyr Ala Ile Gln Val Leu Asp Glu Leu Thr Asp Gly Lys Ala
    450                 455                 460
Ile Ile Ser Thr Gly Val Gly Gln His Gln Met Trp Ala Ala Gln Phe
465                 470                 475                 480
Tyr Lys Tyr Arg Lys Pro Arg Gln Trp Leu Ser Ser Ser Gly Leu Gly
                485                 490                 495
Ala Met Gly Phe Gly Leu Pro Ala Ala Ile Gly Ala Ser Val Ala Asn
            500                 505                 510
Pro Asp Ala Ile Val Val Asp Ile Asp Gly Asp Gly Ser Phe Ile Met
        515                 520                 525
Asn Val Gln Glu Leu Ala Thr Ile Arg Val Glu Asn Leu Pro Val Lys
    530                 535                 540
Val Leu Leu Leu Asn Asn Gln His Leu Gly Met Val Met Gln Trp Glu
545                 550                 555                 560
Asp Arg Phe Tyr Lys Ala Asn Arg Ala His Thr Tyr Leu Gly Asp Pro
                565                 570                 575
Ala Lys Glu Asn Glu Ile Phe Pro Asn Met Leu Gln Phe Ala Gly Ala
            580                 585                 590
```

```
Cys Gly Ile Pro Ala Ala Arg Val Thr Lys Lys Glu Glu Leu Arg Asp
            595                 600                 605

Ala Ile Gln Thr Met Leu Asp Thr Pro Gly Pro Tyr Leu Leu Asp Val
    610                 615                 620

Ile Cys Pro His Gln Glu His Val Leu Pro Met Ile Pro Ser Gly Gly
625                 630                 635                 640

Thr Phe Lys Asp Val Ile Thr Glu Gly Asp Gly Arg Thr Lys Tyr
                645                 650                 655

<210> SEQ ID NO 14
<211> LENGTH: 2024
<212> TYPE: DNA
<213> ORGANISM: Brassica juncea

<400> SEQUENCE: 14
```

| | | | | | |
|---|---|---|---|---|---|
| cacgttcaca | aactcattca | tcatctctcg | ctcatttctc | tccctctcct | ctaaccatgg | 60 |
| cggcggcaac | atcgtcttct | ccaatctcct | tcaccgctaa | accttcttcc | aaatcccttt | 120 |
| tacccatttc | cagattctcc | cttcccttct | ccttaatccc | gcagaaaccc | tcctcccttc | 180 |
| gccacagtcc | tctctccatc | tcagccgttc | tcaacacacc | cgtcaatgtc | gcacctcctt | 240 |
| cccctgaaaa | aattgaaaag | aacaagactt | tcatctcccg | ctacgctccc | gacgagcccc | 300 |
| gcaagggcgc | cgatatcctc | gtcgaagccc | tcgagcgtca | aggcgtcgaa | accgtcttcg | 360 |
| cttacccggg | aggtgcttcc | atggagatcc | accaagcctt | aactcgatcc | tctaccatcc | 420 |
| gtaacgtcct | cccccgtcac | gaacaaggag | gagtctttgc | cgccgagggt | tacgctcgtt | 480 |
| cctctggtaa | accgggaatc | tgcatagcca | cgtcaggtcc | cggagccacc | aacctcgtta | 540 |
| gcggtttagc | cgacgcgatg | ctcgacagtg | tccctctcgt | cgctattaca | ggacaggtcc | 600 |
| ctcgtcggat | gattggtact | gacgcgttcc | aggagacgcc | aatcgttgag | gtaacgaggt | 660 |
| ctattacgaa | acataactat | ctggtcatgg | atgttgatga | catacctagg | atcgtgcaag | 720 |
| aggctttctt | tctagctact | tccggtagac | ccggaccggt | tttagttgat | gttcctaagg | 780 |
| atattcagca | gcagcttgcg | attcctaact | gggatcagcc | tatgcgctta | cctggttaca | 840 |
| tgtctaggct | gcctcagcct | ccggaagttt | ctcagttagg | gcagatcgtt | aggttgatct | 900 |
| ctgaatctaa | gaggcctgtt | ttgtatgttg | gtggtggaag | cttgaactcg | agtgatgaac | 960 |
| tggggaggtt | tgtggagctt | actgggatcc | ctgtcgcgag | tactttgatg | gggcttggtt | 1020 |
| cttatccttg | taacgatgag | ttgtctctgc | agatgcttgg | tatgcacggg | actgtgtacg | 1080 |
| ctaattacgc | tgtggagcat | agtgatttgt | tgctggcgtt | tggtgttagg | tttgatgacc | 1140 |
| gtgtcactgg | aaagctcgag | gcttttgcga | gcagggctaa | gattgtgcac | attgacattg | 1200 |
| attctgctga | gattgggaag | aacaagacgc | tcatgtgtc | tgtgtgtggt | gatgttaagc | 1260 |
| tggctttgca | agggatgaac | aaggttcttg | agaaccgagc | agaggagctc | aagcttgact | 1320 |
| tcggagtttg | gaggagtgaa | ttgagcgagc | agaaacaaaa | gttcccgttg | agttttaaaa | 1380 |
| cgtttggaga | agctattcct | ccacagtacg | cgattcaggt | cctcgacgag | ctaaccgatg | 1440 |
| ggaaggcaat | catcagtact | ggtgttgggc | aacatcagat | gtgggcggcg | cagttttaca | 1500 |
| agtacaggaa | gccgaggcag | tggttgtcat | catcaggcct | tggagctatg | gttttggac | 1560 |
| ttcctgctgc | cattggagcg | tctgtggcga | accctgatgc | gattgttgtg | acattgacg | 1620 |
| gtgacggaag | cttcatcatg | aatgttcaag | agctggccac | aatccgtgta | gagaatcttc | 1680 |
| ctgtgaaggt | actcttgtta | aacaaccagc | atcttggcat | ggttatgcaa | tgggaagatc | 1740 |
| ggttctacaa | agctaacaga | gctcacactt | atctcgggga | tccggcaaag | gagaacgaga | 1800 |

-continued

```
tcttcccaaa catgctgcag tttgcaggag cctgtgggat ccagctgcg agggtgacga    1860 agaaagaaga actccgagat gctattcaga caatgctgga tacaccagga ccatacctgt    1920
tggatgtgat ctgtccgcac caagagcatg tgttaccgat gatcccaaat ggtggtactt    1980
tcaaagatgt cataacagaa ggggatggtc gcactaagta ctga                     2024
```

<210> SEQ ID NO 15
<211> LENGTH: 655
<212> TYPE: PRT
<213> ORGANISM: Brassica juncea

<400> SEQUENCE: 15

```
Met Ala Ala Ala Thr Ser Ser Pro Ile Ser Phe Thr Ala Lys Pro
  1               5                  10                  15

Ser Ser Lys Ser Leu Leu Pro Ile Ser Arg Phe Ser Leu Pro Phe Ser
             20                  25                  30

Leu Ile Pro Gln Lys Pro Ser Ser Leu Arg His Ser Pro Leu Ser Ile
         35                  40                  45

Ser Ala Val Leu Asn Thr Pro Val Asn Val Ala Pro Pro Ser Pro Glu
     50                  55                  60

Lys Ile Glu Lys Asn Lys Thr Phe Ile Ser Arg Tyr Ala Pro Asp Glu
 65                  70                  75                  80

Pro Arg Lys Gly Ala Asp Ile Leu Val Glu Ala Leu Glu Arg Gln Gly
                 85                  90                  95

Val Glu Thr Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125

Glu Gln Gly Gly Val Phe Ala Ala Glu Gly Tyr Ala Arg Ser Ser Gly
    130                 135                 140

Lys Pro Gly Ile Cys Ile Ala Thr Ser Gly Pro Gly Ala Thr Asn Leu
145                 150                 155                 160

Val Ser Gly Leu Ala Asp Ala Met Leu Asp Ser Val Pro Leu Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Met Asp Val Asp Ile Pro Arg Ile Val Gln Glu Ala Phe
    210                 215                 220

Phe Leu Ala Thr Ser Gly Arg Pro Gly Pro Val Leu Val Asp Val Pro
225                 230                 235                 240

Lys Asp Ile Gln Gln Gln Leu Ala Ile Pro Asn Trp Asp Gln Pro Met
                245                 250                 255

Arg Leu Pro Gly Tyr Met Ser Arg Leu Pro Gln Pro Pro Glu Val Ser
            260                 265                 270

Gln Leu Gly Gln Ile Val Arg Leu Ile Ser Glu Ser Lys Arg Pro Val
        275                 280                 285

Leu Tyr Val Gly Gly Gly Ser Leu Asn Ser Ser Asp Glu Leu Gly Arg
    290                 295                 300

Phe Val Glu Leu Thr Gly Ile Pro Val Ala Ser Thr Leu Met Gly Leu
305                 310                 315                 320

Gly Ser Tyr Pro Cys Asn Asp Glu Leu Ser Leu Gln Met Leu Gly Met
                325                 330                 335
```

His Gly Thr Val Tyr Ala Asn Tyr Ala Val Glu His Ser Asp Leu Leu
            340                 345                 350

Leu Ala Phe Gly Val Arg Phe Asp Asp Arg Val Thr Gly Lys Leu Glu
            355                 360                 365

Ala Phe Ala Ser Arg Ala Lys Ile Val His Ile Asp Ile Asp Ser Ala
370                 375                 380

Glu Ile Gly Lys Asn Lys Thr Pro His Val Ser Val Cys Gly Asp Val
385                 390                 395                 400

Lys Leu Ala Leu Gln Gly Met Asn Lys Val Leu Glu Asn Arg Ala Glu
            405                 410                 415

Glu Leu Lys Leu Asp Phe Gly Val Trp Arg Ser Glu Leu Ser Glu Gln
            420                 425                 430

Lys Gln Lys Phe Pro Leu Ser Phe Lys Thr Phe Gly Glu Ala Ile Pro
            435                 440                 445

Pro Gln Tyr Ala Ile Gln Val Leu Asp Glu Leu Thr Asp Gly Lys Ala
            450                 455                 460

Ile Ile Ser Thr Gly Val Gly Gln His Gln Met Trp Ala Ala Gln Phe
465                 470                 475                 480

Tyr Lys Tyr Arg Lys Pro Arg Gln Trp Leu Ser Ser Ser Gly Leu Gly
            485                 490                 495

Ala Met Gly Phe Gly Leu Pro Ala Ala Ile Gly Ala Ser Val Ala Asn
            500                 505                 510

Pro Asp Ala Ile Val Val Asp Ile Asp Gly Asp Gly Ser Phe Ile Met
            515                 520                 525

Asn Val Gln Glu Leu Ala Thr Ile Arg Val Glu Asn Leu Pro Val Lys
            530                 535                 540

Val Leu Leu Leu Asn Asn Gln His Leu Gly Met Val Met Gln Trp Glu
545                 550                 555                 560

Asp Arg Phe Tyr Lys Ala Asn Arg Ala His Thr Tyr Leu Gly Asp Pro
            565                 570                 575

Ala Lys Glu Asn Glu Ile Phe Pro Asn Met Leu Gln Phe Ala Gly Ala
            580                 585                 590

Cys Gly Ile Pro Ala Ala Arg Val Thr Lys Lys Glu Glu Leu Arg Asp
            595                 600                 605

Ala Ile Gln Thr Met Leu Asp Thr Pro Gly Pro Tyr Leu Leu Asp Val
            610                 615                 620

Ile Cys Pro His Gln Glu His Val Leu Pro Met Ile Pro Asn Gly Gly
625                 630                 635                 640

Thr Phe Lys Asp Val Ile Thr Glu Gly Asp Gly Arg Thr Lys Tyr
            645                 650                 655

<210> SEQ ID NO 16
<211> LENGTH: 15
<212> TYPE: DNA
<213> ORGANISM: Brassica juncea

<400> SEQUENCE: 16
atcccaagtg gtggt                                                    15

<210> SEQ ID NO 17
<211> LENGTH: 15
<212> TYPE: DNA
<213> ORGANISM: Brassica junca

<400> SEQUENCE: 17

```
atcccaaatg gtggt                                                    15

<210> SEQ ID NO 18
<211> LENGTH: 15
<212> TYPE: DNA
<213> ORGANISM: Arabidopsis thaliana

<400> SEQUENCE: 18
atcccgagtg gtggc                                                    15

<210> SEQ ID NO 19
<211> LENGTH: 15
<212> TYPE: DNA
<213> ORGANISM: Arabidopsis thaliana

<400> SEQUENCE: 19
atcccgaatg gtggc                                                    15

<210> SEQ ID NO 20
<211> LENGTH: 5
<212> TYPE: PRT
<213> ORGANISM: Brassica juncea

<400> SEQUENCE: 20

Ile Pro Ser Gly Gly
1               5

<210> SEQ ID NO 21
<211> LENGTH: 5
<212> TYPE: PRT
<213> ORGANISM: Brassica juncea

<400> SEQUENCE: 21

Ile Pro Asn Gly Gly
1               5

<210> SEQ ID NO 22
<211> LENGTH: 5
<212> TYPE: PRT
<213> ORGANISM: Arabidopsis thaliana

<400> SEQUENCE: 22

Ile Pro Ser Gly Gly
1               5

<210> SEQ ID NO 23
<211> LENGTH: 5
<212> TYPE: PRT
<213> ORGANISM: Arabidopsis thaliana

<400> SEQUENCE: 23

Ile Pro Asn Gly Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Consensus Sequence

<400> SEQUENCE: 24

Gly Ala Ser Met Glu Ile His Gln
1               5
```

```
<210> SEQ ID NO 25
<211> LENGTH: 8
<212> TYPE: PRT
<213> ORGANISM: Brassica napus

<400> SEQUENCE: 25

Glu Gly Asp Gly Arg Thr Lys Tyr
1               5
```

BRASSICA AHAS GENES AND GENE ALLELES THAT PROVIDE RESISTANCE TO IMIDAZOLINONE HERBICIDES

CROSS-REFERENCE TO RELATED APPLICATIONS

This application is a divisional of U.S. application Ser. No. 11/079,122, filed Mar. 14, 2005, which claims the benefit of U.S. Provisional Application No. 60/581,315, filed Jun. 22, 2004, both of which are hereby incorporated herein in their entirety by reference.

FIELD OF THE INVENTION

All publications cited in this application are herein incorporated by reference.

The invention is in the field of improved lines of *Brassica*, including *Brassica juncea*, improved imidazolinone herbicide resistant *B. juncea*, methods for generation of such lines, and methods for selection of such lines. More specifically, certain embodiments relate to *Brassica* AHAS genes and sequences and a gene allele bearing a point mutation that gives rise to imidazolinone herbicide resistance.

BACKGROUND OF THE INVENTION

*B. juncea* is grown in many countries of the world for the production of mustard and edible oil. Mustard quality genotypes of *B. juncea* are high in glucosinolate and erucic acid content. Some genotypes have been developed which are low in glucosinolate and erucic acid content, these are referred to as "canola quality" and are preferred for edible oil consumption. *Brassica napus* and *B. rapa* are other *Brassica* species that have been developed to produce canola oil. To be classified as canola, genotypes must have an erucic acid content of less than two percent in the oil and a glucosinolate content of less than 30 micromoles per gram of meal.

The genetic relationship among the *Brassica* species was described by U (1935). There are three diploid species, with the genome of *B. rapa* designated as 'A', the genome of *B. nigra* designated as 'B' and the genome of *B. oleracea* designated as 'C'. There are three allotetraploid species in which the diploid genomes are combined. Thus, *B. juncea* has an AB genomic constitution by combining the genomes of *B. rapa* and *B. nigra*, *B. napus* has AC from *B. rapa* and *B. oleracea*, and *B. carinata* has BC from *B. nigra* and *B. oleracea*. During meiosis, the chromosomes from each genome will pair with their homologues, thus in *B. juncea*, A chromosomes will pair with A and B will pair with B. Interspecific crosses can be made between *Brassica* species, but progeny of the cross will be sterile. In a cross between *B. juncea* and *B. napus*, for example, the common A chromosomes will pair, but the B and C chromosomes will not pair well, causing sterility. Crossing back to either species can restore fertility, but the alien genome chromosomes are lost. For this reason, it is very difficult to get genetic transfer between chromosomes of different genomes, for example from the C genome of *B. napus* to the B genome of *B. juncea*.

The allotetraploid species have homologous genes on the two genomes. For example, acetohydroxy acid synthase (AHAS), the first enzyme in the synthesis of the amino acids leucine, isoleucine and valine, is encoded by multiple gene members of a small gene family that are designated as AHAS genes. Rutledge et al. (Mol Gen Genet 229: 31-40, 1991) characterized the AHAS genes in *B. napus*. They found five AHAS genes, with AHAS2, AHAS3 and AHAS4 on the A genome and with AHAS1 and AHAS5 on the C genome. AHAS1 and AHAS3 are 98% homologous within their coding regions. Gene expression analysis by Ouellet et al., (Plant J. 2: 321-330, 1992) indicated that AHAS1 and AHAS3 are expressed at all growth stages and are the most important for normal growth. AHAS2 is active only in mature ovules and extra-embryonic tissues of immature seeds. AHAS4 and AHAS5 are not expressed in *B. napus*.

Herbicide tolerance is a desired attribute in commercial varieties of the *Brassica* genus including *B. napus*, *B. rapa* and *B. juncea*. Herbicide tolerance provides an economically viable method to control a wide range of weeds in the crop. Weeds such as stinkweed, wild mustard, flixweed, ball mustard and shepard's purse are closely related to *B. juncea* and therefore difficult to control with herbicides without damaging the crop. With an herbicide tolerant variety, it is possible to control other varieties of the same species which do not possess the trait and thereby keep the variety pure. Imidazolinone herbicides affect amino acid biosynthesis in susceptible plants by disrupting activity of the AHAS enzyme. Resistance to imidazolinone herbicides has been developed in *B. napus* varieties of canola. Mutations in the AHAS coding regions alter the enzyme structure and prevent inhibition of the enzyme by the herbicide. Swanson et al. (Plant Cell Rep 7:83-87, 1988) reported the discovery of *B. napus* plants with mutations conferring tolerance to imidazolinone and sulfonylurea herbicides. Through sequence analysis, the mutation responsible for resistance to imidazolinones was identified as a single basepair change (G to A) in the 3' end of the AHAS gene of the *Arabidopsis* mutant imr1, which caused an amino acid change from Ser to Asn (Sathasivan et al., Plant Physiol. 97:104-41050, 1991; Hattori et al., Mol. Gen. Genet. 232: 167-173, 1992). In *Brassica napus*, the mutation responsible for resistance to multiple herbicides, including the imidazolinones, was identified as a single basepair change (G to T) in the 3' end of AHAS3 causing an amino acid change from Trp to Leu (Hattori et al., Mol. Gen. Genet. 246: 419-425, 1995).

Gingera et al. (U.S. Pat. No. 6,613,963) disclose three *B. juncea* lines with tolerance to imidazolinone herbicides derived from an interspecific cross between *B. juncea* and a tolerant *B. napus* variety, followed by three backcrosses to *B. juncea*. It is disclosed that the plants were tolerant to herbicide applied at the usual field rate. No molecular information is provided regarding how many mutated *B. napus* genes were actually transferred and, if both mutated genes transferred, where they are located in the *B. juncea* genomes. Since *B. juncea* and *B. napus* share the A genome, it would presumably be simple to transfer the mutated AHAS3 gene located on the A genome. It will be much more difficult to transfer the mutant AHAS1 gene from the C genome of *B. napus* to the B genome of *B. juncea*. When backcrossing to *B. juncea*, there will be a tendency to have B genome chromosomes replace the C chromosomes and thus the mutated AHAS1 gene will be lost. Selection for herbicide tolerance was carried out at each stage, but according to Swanson et al. (Theor Appl Genet 78:525-530, 1989), the mutated AHAS3 gene on the A genome alone will provide tolerance to the usual field rate of herbicide. Thus, without the type of molecular information regarding the *B. juncea* AHAS gene sequences provided by this current invention, there would be no way to confirm that the mutated AHAS1 gene from *B. napus* was successfully transferred to *B. juncea*. While the mutated AHAS1 and AHAS3 genes together will act additively to provide enhanced tolerance to imidazolinone herbicides (Swanson et al., Theor Appl Genet 78:525-530, 1989), this will not be apparent at the herbicide rate disclosed by Gingera et al.

There remains a need for a *B. juncea* variety with a mutation in the AHAS1 gene on the B genome and a method to identify plants containing the mutant allele, especially in plants which already have a mutated AHAS3 gene. In this invention, we disclose information regarding creation of imidazolinone resistant *B. juncea* line J04E-0044, deposited as ATCC Accession Number PTA-6324, the mutant AHAS gene allele on the B genome of *B. juncea* line J04E-0044 (BjAHAS-bR) and selection methods for determining the presence of the mutant allele. It is obvious that the mutant allele of the B genome AHAS gene (BjAHAS-bR) is more likely to be stable than the AHAS1 mutant allele introgressed from *B. napus*.

SUMMARY OF THE INVENTION

The invention comprises *Brassica* seeds, plants, plant parts and plant lines that are resistant to imidazolinone herbicides. The seeds, plants, plant parts and plant lines disclosed in the invention have imidazolinone herbicide-resistant AHAS activity. Specifically, *B. juncea* line J04E-0044 (ATCC Accession Number PTA-6324) disclosed in the invention has a mutation in one of the AHAS gene loci, which confers the imidazolinone herbicides-resistant AHAS activity. Also disclosed in this invention is the confirmation that the mutant AHAS gene allele (BjAHAS-bR) is at the same gene locus of the wild type AHAS gene allele BjAHAS-b belonging to the B genome of *B. juncea*.

Some embodiments of the invention are isolated nucleic acid fragments comprising nucleotide sequences encoding various *Brassica* AHAS genes including BjAHAS-a from *B. juncea* A genome, BjAHAS-b from *B. juncea* B genome and BngrAHAS from *B. nigra*. One specific embodiment of the invention is an isolated nucleic acid fragment comprising a nucleotide sequence encoding the mutant allele BjAHAS-bR conferring imidazolinone herbicide resistance, which was isolated from *B. juncea* line J04E-0044 (ATCC Accession Number PTA-6324).

A further embodiment of the invention involves a method of producing a *Brassica* plant line comprising the steps of: (a) inducing mutagenesis in cells of a starting variety of a *Brassica* species; (b) obtaining progeny plants from the mutagenized cells; (c) identifying progeny plants that are resistant to imidazolinone herbicides and that have the desired mutant allele of AHAS gene, BjAHAS-bR; and (d) producing a plant line by selfing or crossing.

Another embodiment of the invention involves a method of producing *Brassica* plant lines that are resistant to imidazolinone herbicides and that have the desired mutant allele BjAHAS-bR comprising steps of (a) making a cross involving a first parent plant that is resistant to imidazolinone herbicides and that has the desired mutant allele BjAHAS-bR and a second parent plant; (b) obtaining seeds from the cross of step (a); (c) growing fertile plants from such seeds; (d) identifying progeny plants that are resistant to imidazolinone herbicides and that have the desired mutant allele BjAHAS-bR; and (e) obtaining progeny seeds from the such selected plants of step (d).

BRIEF DESCRIPTION OF THE FIGURES

FIG. 2 shows a comparison of the DNA and the deduced amino acid sequences of the wild type allele BjAHAS-b and the mutant allele BjAHAS-bR. The *Arabidopsis* AHAS gene (AtAHAS) and the corresponding mutant allele imr1 are included for reference. Single letters are used for amino acids: I, Isoleucine; P, Proline; S, Serine; N, Asparagine; G, Glycine. Wild type allele codon AGT and its coded amino acid S and mutant allele codon AAT and its coded amino acid N are underlined.

BRIEF DESCRIPTION OF THE SEQUENCE LISTING

Figure 1:
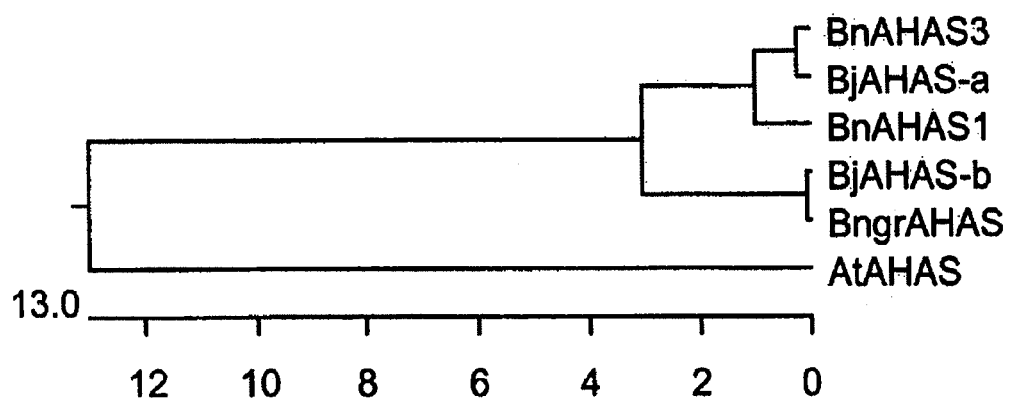
FIG. 1 shows a phylogenetic analysis of the relationships among selected *Brassica* AHAS genes using nucleotide sequences, which were aligned by the CLUSTAL program. BjAHAS-b, *B. juncea* AHAS gene from the B genome (this invention); BngrAHAS, *Brassica nigra* AHAS gene (B genome) (this invention); BjAHAS-a, *B. juncea* AHAS gene from the A genome (this invention); BnAHAS3, *Brassica napus* AHAS3 (A genome; GenBank Accession # Z11526); *Brassica napus* AHAS1 (C genome; GenBank Accession # Z11524); AtAHAS, *Arabidopsis* AHAS gene (GenBank Accession # AY042819). The scale beneath the phylogenetic tree indicates the distance between sequences.

SEQ ID NO:1 shows primer KY33 for PCR amplification of AHAS genes.

SEQ ID NO:2 shows primer KY34 for PCR amplification of AHAS genes.

SEQ ID NO:3 shows primer KY35 used for 3' RACE to amplify the 3' end of AHAS genes.

SEQ ID NO:4 shows primer Uni-T17 used for 3' RACE to amplify the 3' end of AHAS genes.

SEQ ID NO:5 shows primer Uni used for 3' RACE to amplify the 3' end of AHAS genes.

SEQ ID NO:6 shows primer KY33A used to amplify the 5' end of the AHAS genes.

SEQ ID NO:7 shows primer KY36 used to amplify the 5' end of the AHAS genes.

SEQ ID NO:8 shows the BjAHAS-a gene Isolated from the A genome of *B. juncea*.

SEQ ID NO:9 shows the BjAHAS-b gene isolated from the B genome of *B. juncea*.

SEQ ID NO:10 shows the BngrAHAS gene isolated from *B. nigra*.

SEQ ID NO:11 is the deduced amino acid sequence of SEQ ID NO. 8.

SEQ ID NO:12 is the deduced amino acid sequence of SEQ ID NO. 9.

SEQ ID NO:13 is the deduced amino acid sequence of SEQ ID NO. 10.

SEQ ID NO:14 shows the mutant allele BjAHAS-bR isolated from the B genome of *B. juncea* mutant line J04E-0044.

SEQ ID NO:15 is the deduced amino acid sequence of SEQ ID NO. 14.

SEQ ID NO:16 shows the wild-type allele of BjAHAS-b.

SEQ ID NO:17 shows the mutant allele of BjAHAS-bR.

SEQ ID NO:18 shows the AHAS allele of *Arabidopsis*.

SEQ ID NO:19 shows the mutant allele imr1.

SEQ ID NO:20 shows the amino acid sequence for wild-type BjAHAS-b.

SEQ ID NO:21 shows the amino acid sequence for the mutant allele of BjAHAS-bR.

SEQ ID NO:22 shows the amino acid sequence for the *Arabidopsis* AHAS allele.

SEQ ID NO:23 shows the amino acid sequence for the imr1 mutant allele.

DEFINITIONS

For clarity of description, some of the terminology used in this application is explained as follows.

Brassica. The term "*Brassica*" may comprise any or all of the species subsumed in the genus *Brassica* including *Brassica napus, Brassica juncea*, and *Brassica rapa*. Although the specific embodiments disclosed generally refer to *Brassica juncea*, it is understood that some or all may be adaptable to one or more of the other species of *Brassica*.

Breeding. "Breeding" includes all methods of developing or propagating plants and includes both intra- and inter-species and intra- and inter-line crosses as well as all suitable artificial breeding techniques. Desired traits may be transferred to other *B. juncea* lines through conventional breeding methods and can also be transferred to other *Brassica* species, such as *B. napus* and *B. rapa* through inter-specific crossing. Both conventional breeding methods and inter-specific crossing methods as well as other methods of transferring genetic material between plants are well documented in the literature.

Genetically derived. The term "genetically derived" as used, for example, in the phrase "genetically derived from the parent lines" means that the characteristic in question is dictated wholly or in part by an aspect of the genetic makeup of the plant in question.

Heterozygosity. The term "heterozygosity" (H) is used when a fraction of individuals in a population have different alleles at a particular locus (as opposed to two copies of the same allele). Heterozygosity is the probability that an individual in the population is heterozygous at the locus. Heterozygosity is usually expressed as a percentage (%), ranging from 0 to 100%, or on a scale from 0 to 1.

Homozygosity. "Homozygosity" or "homozygous" indicates that a fraction of individuals in a population have two copies of the same allele at a particular locus. Where plants are doubled haploid it is presumed that subject to any spontaneous mutations occurring during duplication of the haplotype, all loci are homozygous. Plants may be homozygous for one, several or all loci as the context indicates.

Hybridization. "Hybridization" refers to a process in which a strand of nucleic acid joins with a complementary strand through base pairing. Polynucleotides are "hybridizable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementation over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementation between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

Isolated. An "isolated" nucleic acid or polynucleotide as used herein refers to a component that is removed from its original environment (for example, its natural environment if it is naturally occurring). An isolated nucleic acid or polypeptide may contain less than about 50%, less than about 75%, less than about 90%, less than about 95%, less than about 99.9% and less than any integer value between 50 and 99.9% of the cellular components with which it was originally associated. A polynucleotide amplified using PCR so that it is sufficiently distinguishable (on a gel from example) from the rest of the cellular components may, for example, be considered "isolated". The polynucleotides of the invention may be "substantially pure," i.e., having the highest degree of purity that can be achieved using a particular purification technique known in the art.

Line. A "line" refers to a group of plants that display little or no genetic variation between individuals for at least one trait. A "DH (doubled haploid) line", as used here refers to a group of plants generated by culturing a haploid tissue and then doubling the chromosome content without accompanying cell division, to yield a plant with the diploid number of chromosomes where each chromosome pair is comprised of two duplicated chromosomes. Therefore, a DH line normally displays little or no genetic variation between individuals for traits.

$M_0$, $M_1$, $M_2$. "$M_0$" refers to untreated seeds; "$M_1$" refers to the seeds exposed to mutagenesis and the resulting plants; "$M_2$" refers to the progeny (seeds and plants) of self-pollinated $M_1$ plants; "$M_3$" refers to the progeny (seeds and plants) of self-pollinated $M_2$ plants; "$M_4$" refers to the progeny (seeds and plants) of self-pollinated $M_3$ plants; "$M_5$" refers to the progeny (seeds and plants) of self-pollinated $M_4$ plants, and so on.

Molecular biological techniques. "Molecular biological techniques" means all forms of manipulation of a nucleic acid sequence to alter the sequence and expression thereof and includes the insertion, deletion or modification of sequences or sequence fragments and the direct introduction of new sequences into the genome of an organism by directed or random recombination using any suitable vectors and/or techniques.

Mutagenesis. The term "mutagenesis" means a process of inducing random or directed genetic mutations within a population of individuals. A mutagenic agent is an agent suitable to cause mutagenesis. Possible mutagenic techniques include but are not limited to treatment with chemical mutagens, irradiation treatment and any other techniques that may induce mutations. Suitable mutagens may include EMS or any other chemical, radiation or other treatment, which has the effect of causing changes to the genetic material. In some cases, the genetic changes produce viable plants but if they lack desired traits they can be discarded. If changes create a desired trait but are linked to an unwanted trait, the desired trait may be transferable to other plants through conventional breeding techniques or by artificial genetic manipulation.

Polymorphism. "Polymorphism" is a condition in DNA in which the most frequent variant (or allele) has a population frequency which does not exceed 99%.

Primers. "Primers" are short polynucleotides or oligonucleotides required for a polymerase chain reaction that are complementary to a portion of the polynucleotide to be amplified. For example, the primer may be no more than 50 nucleotides long, preferably less than about 30 nucleotides long, and most preferably less than about 24 nucleotides long.

Progeny. "Progeny" means the direct and indirect descendants, offspring and derivatives of a plant or plants and includes the first, second, third and subsequent generations and may be produced by self-crossing, crossing with plants with the same or different genotypes, and may be modified by a range of suitable genetic engineering techniques.

Recombinant. Various genes and nucleic add sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention. Recombinant nucleic acid constructs may, for example, be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cell, or as the result of subsequent recombination and/or repair events.

Substantial homology. Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 91%, 92%, 93%, 94%, 95%, 96%, 97%, 98%, 99%, or 100% sequence identity wherein the percent sequence identity is based on the entire sequence and is determined by GAP alignment using default parameters (GCG, GAP version 10, Accelrys, San Diego, Calif.). GAP uses the algorithm of Needleman and Wunsch (*J. Mol. Biol.* 48:443-453, 1970) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully complementary.

DETAILED DESCRIPTION OF THE INVENTION

There is disclosed in this invention a *Brassica* plant which may be *B. juncea* that is resistant to wide-spectrum herbicides including imidazolinone herbicides. In one embodiment the *Brassica* plant may be *B. juncea* and may be *B. juncea* line J04E-0044. In another embodiment of the invention the *Brassica* plant which may be *B. juncea* and may be J04E-0044 was created by means of a mutation. The current invention, the *B. juncea* line J04E-0044 containing mutant allele BjAHAS-bR, has been deposited under the ATCC Accession Number PTA-6324 at the American Type Culture Collection of 10801 University Blvd., Manassas, Va., 20110-2209, U.S.A., under the terms of the Budapest Treaty.

As one embodiment of the invention, there is disclosed a method for creating plants that are resistant to herbicides including imidazolinone herbicides comprising: (a) inducing mutagenesis in at least some cells from a *Brassica* line; (b) regenerating plants from at least one of the mutagenized cells and selecting regenerated plants that are resistant to herbicides such as imidazolinone herbicides; (c) deriving further generations of herbicide resistant plants from said regenerated plants and individuals of the said further generations of plants that are herbicide resistant. In some embodiments, the *Brassica* may be *B. juncea*. The selection of herbicide resistant individual plants at each generation is accomplished by spraying the imidazolinone herbicide Odyssey® at a rate of 42 g of the active ingredient per hectare.

As another embodiment of the invention there are disclosed *Brassica* plants, which may be *B. juncea* line J04E-0044 containing herbicide resistant AHAS enzyme activity. In one related embodiment, the herbicide imidazolinone is used as the AHAS activity inhibitor. *B. juncea* variety 'Arid', which was used for creating the *B. juncea* line J04E-0044 by mutagenesis, is used as a susceptible check. In the presence of an imidazolinone herbicide, Arid has less than 2% AHAS activity than without the inhibitor. In contrast, J04E-0044 has significantly higher relative AHAS activities. In certain exemplary embodiments, J04E-0044 has relative AHAS activity of 70%, 79% or 91% (Table 1).

In another embodiment of the invention, there is disclosed a *Brassica* plant, which may be *Brassica juncea*, comprising the BjAHAS-bR mutant allele at the BjAHAS-b gene locus, which is located on the B genome of *B. juncea*. In certain embodiments the plant may be homozygous for the BjAHAS-b gene locus as BjAHAS-bR allele. In a specific embodiment, the BjAHAS-b gene locus encodes, together with the BjAHAS-a gene locus, active AHAS enzymes. In a related embodiment, J04E-0044 has a mutation at its BjAHAS-b gene locus.

In a further embodiment of the invention, there is disclosed isolated nucleic acid molecules comprising sequences of *B. juncea* AHAS genes, BjAHAS-a (SEQ ID NO. 8) and BjAHAS-b (SEQ ID NO. 9). Through sequence comparison, it is confirmed that BjAHAS-a and BjAHAS-b belong to the A genome and the B genome, respectively, of *B. juncea*. Also disclosed in the current invention is the isolated nucleic acid molecule comprising a sequence of *B. nigra* AHAS gene, BngrAHAS (SEQ ID NO. 10). BjAHAS-a and the *B. napus* AHAS3 are highly homologous (99.6% nucleotide sequence identity). BjAHAS-b and *B. napus* AHAS1 are also homologous but with a decreased percentage in nucleotide sequence identity (94.1% nucleotide sequence identity). The above isolated molecule may be DNA, RNA or any other genetically useable nucleic acid. The isolated nucleic acid molecule may further comprise a bacterial plasmid or other cloning vector, virus or the like. Homology may be detectable by hybridization with appropriate nucleic acid probes, by PCR techniques with suitable primers or by any other commonly used techniques.

In another embodiment of the invention there is disclosed a *Brassica* plant, which may be *Brassica juncea*, comprising the BjAHAS-bR mutant allele at the BjAHAS-b gene locus, which confers herbicide resistance. In a related embodiment of the invention there is disclosed a *Brassica* plant, which may be *B. juncea*, comprising the BjAHAS-bR mutant allele at the BjAHAS-b gene locus, which confers herbicide resistant AHAS activity. In an exemplary embodiment, the herbicide is imidazolinone.

In a particular embodiment BjAHAS-bR mutant allele is heritable. In some other embodiments the desired allele may be introduced into other *Brassica* plants by breeding techniques and in others it may be introduced by molecular biological techniques, such as recombinant DNA techniques and plant transformation.

In one embodiment there is disclosed a process of producing a genetically stable *Brassica* plant that may be *B. juncea* that is resistant to herbicides such as imidazolinone. The process may comprise the steps of: crossing J04E-0044 with other *Brassica* plants to form F1 progeny; and propagating the progeny by means that may include self-pollination or the development of doubled haploid plants; and, from the resulting progeny, selecting genetically stable plants that generate seeds having the desired mutant allele BjAHAS-bR.

Another embodiment of the current invention is to provide a method of designing a genetic marker for the mutated allele BjAHAS-bR which would be useful for selecting plants carrying the mutation. In a specific embodiment disclosed in the current invention, the specific single base-pair change (G to A) of the mutant allele provides valuable information for designing an allele-specific PCR primer involving a 3' mismatch. It is understood that various primer combinations can be made, which is up to the preference of the designer who is skilled in the art. In various aspects of the present invention, the allele-specific PCR primers could be forward primers or reverse primers with a "G/C" at its 3' end (for wild type allele) or an "A/T" at its 3' end (for mutant allele). For a summary of allele-specific PCR, see publications by Myakishev et al., 2001 (Genome Research 11: 163-169) and Tanhuanpää et al., 1999 (Molecular Breeding 4: 543-550).

In a particular embodiment there is provided nucleic acid probes which may comprise sequences comprising, or homologous to, portions of the BjAHAS-bR allele and further embodiments may include the use of suitable primer pairs to amplify or detect the presence of the allele BjAHAS-bR.

In a related embodiment it is understood that various methods for detecting single nucleotide polymorphisms (SNPs) could also be used for identifying the BjAHAS-bR mutant allele. These methods may include, but are not limited to, TaqMan assay and Molecular Beacon assay (Täpp et al., BioTechniques 28: 732-738), Invader Assays (Mein et al., Genome Research 10: 330-343, 2000) and single strand conformational polymorphism (SSCP) (Orita et al., Proc. Natl. Acad. Sci. U.S.A. 86: 2766-2770, 1989).

It will be readily apparent to those persons skilled in the art that plants of the current invention may be used in crosses with plants containing other AHAS gene mutations to combine the mutations and provide even greater herbicide tolerance. For example, plants of the current invention could be crossed with plants containing a mutated AHAS3 gene on the A genome, obtained through an interspecific cross with a *B. napus* variety carrying the mutation. Since *B. juncea* and *B. napus* share the A genome, transfer of the mutated AHAS3 gene will be relatively straightforward to those skilled in the art. See also Gingera et al. (U.S. Pat. No. 6,613,963), Swanson et al. (Theor Appl Genet 78:525530, 1989).

It will be readily apparent to those skilled in the art, that a variety of *B. juncea* of this invention can be combined with other varieties of *B. juncea* or related species to incorporate a wide range of attributes, such as, but not limited to: improved oil content, modified fatty acid profile, low glucosinolate content, high tocopherol content, high yield, disease resistance, lodging resistance, shattering resistance, early maturity, improved meal quality and large seed size. Plants or varieties of this invention could also be used as parents of hybrids.

It is understood that various modifications and alternatives can be made to the present invention. Certain specific embodiments thereof are described in the general methods and further explained by the following examples. The invention certainly applies to all canola quality *B. juncea* varieties as well as all non-canola quality *B. juncea* varieties, such as oriental or brown mustard. The invention may be applied to all other *Brassica* species, including *B. nigra* and *B. carinata*, to produce substantially similar results. It should also be understood that these examples are not intended to limit the invention to particular forms disclosed, but instead, the invention is to cover all modifications, equivalents and alternatives falling within the scope of the invention.

Example 1

Creation of Mutagenized *B. juncea* Seed Lines

Seed of *B. juncea* cultivar "Arid" was treated with ethyl methyl sulfonate (EMS) at a concentration of 0.3% for 16 hours. After drying, the seed ($M_1$) was planted and plants were grown to maturity. Seed was harvested ($M_2$) and sown in flats containing Redi-Earth®. Flats were sprayed with a solution containing the imidazolinone herbicide Odyssey®, at a rate of 42 grams of active ingredient per hectare. Ten days after sowing, seedlings showing tolerance to the herbicide were transferred to pots. One such plant was designated as J04E0044, which has been deposited under the ATCC Accession Number PTA6324 at the American Type Culture Collection of 10801 University Blvd., Manassas, Va., 20110-2209, U.S.A., under terms of the Budapest Treaty.

Leaf discs were removed from seedling leaves of J04E-0044 and subjected to an assay of AHAS activity, as described by Singh et al. (Anal. Biochem. 171: 173-179, 1988). The assay measures AHAS activity by estimating the amount of product, acetolactate, after conversion by decarboxylation in the presence of acid to acetoin. The assay compares the AHAS activity in two leaf discs. The control leaf disc was incubated in 10 mM phosphate buffer (pH 6.0) containing 50 mM pyruvate, 500 uM cyclopropane dicarboxylic acid (CPCA), 10% M&S salts and 0.5% alanine. The other leaf disc was in the same buffer in the presence of 2.5 uM imazamox, an imidazolinone herbicide. The herbicide normally binds to the AHAS enzyme and inhibits activity. The incubations were carried out at 22° C. for 16 hrs followed by measuring the absorbance at A530 nm. A completely herbicide susceptible plant will have an AHAS activity level near zero when exposed to an inhibitory herbicide, while a tolerant plant will have AHAS activity nearly equal to that of the control. A plant with a mutated AHAS gene in one genome but not the other will have intermediate AHAS activity in the present of enzyme inhibitor. The procedure was modified to include the addition of cyclopropane dicarboxylic acid (CPCA), which prevents the further conversion of acetolactate to valine and leucine. In addition to an imidazolinone herbicide as an inhibitor, a sulfonylurea herbicide (chlorsulfuron) was also used on separate leaf discs to test for cross-tolerance in the same way except that 0.2 uM chlorsulfuron was used instead of 2.5 uM imazamox. The results of the three assays involving J04E-0044 are presented in Table 1. In this table, the line PM1 is a B. napus variety with a mutation affecting the AHAS1 gene in the C genome only and PM2 is a B. napus variety with a mutation in the AHAS3 gene, located in the A genome. Susceptible check is a commercial B. juncea variety.

The PM2 mutation in the A genome provides tolerance to both imidazolinone and sulfonylurea herbicides, whereas the PM1 mutation provides less tolerance to imidazolinone herbicides and no tolerance to sulfonylurea herbicides. The mutation in B. juncea variety J04E-0044 provides tolerance equal to that of PM2 to the imidazolinone herbicide, but little tolerance to chlorsulfuron.

TABLE 1

Relative AHAS activity of leaf discs exposed to herbicide inhibitors compared to controls.

| Assay # | Variety | Relative AHAS activity with imidazolinone (0-1) | Relative AHAS activity with chlorsulfuron (0-1) |
| --- | --- | --- | --- |
| 1 | Susceptible check | 0.018 | 0.029 |
| 1 | PM1 | 0.276 | 0.057 |
| 1 | PM2 | 0.607 | 0.664 |
| 1 | J04E-0044 | 0.703 | 0.032 |
| 2 | PM1 | 0.256 | 0.004 |
| 2 | PM2 | 0.722 | 0.778 |
| 2 | J04E-0044 | 0.793 | 0.274 |
| 3 | PM1 | 0.292 | 0.015 |
| 3 | J04E-0044 | 0.919 | 0.111 |

Example 2

Cloning of the AHAS Genes from B. juncea and B. nigra

Two degenerate PCR primers were designed in order to PCR amplify and clone AHAS genes from B. juncea and B. nigra. The primer design was under two considerations. First, B. juncea has A and B genomes and B. nigra has the B genome only. Therefore, the AHAS gene from the B genome might be very divergent from the known B. napus AHAS2 and AHAS3 (A genome) and the B. napus AHAS1 (C genome) (Rutledge et al., Mol. Gen. Genet. 229: 31-40, 1991). The second consideration is that the amplification should cover regions where the known mutations of the AHAS genes occur, which gave rise to resistance to various herbicides. These mutations include the Arabidopsis AHAS imr1, a Ser to Asn substitution at aa 653 (Sathasivan et al., Plant Physiol. 97:1044-1050, 1991) and the B. napus AHAS3 PM2, a Trp to Leu substitution at aa 557 (Hattori et al., Mol Gen Genet 246: 419-425, 1995). The forward primer KY33 (5'-GGN GCN TCN ATG GAR ATH CAY CAR-3') (SEQ ID NO. 1) is based on a consensus amino acid sequence (GASMEIHQ; SEQ ID NO: 24) from 4 known plant AHAS protein sequences, i.e. the B. napus AHAS1 (GenBank Accession No. CAA77613), the B. napus AHAS3 (GenBank Accession No. CAA77615), the B. napus AHAS2 (GenBank Accession No. CAA77614), and the Arabidopsis AHAS (GenBank Accession No. 1501386 B). The reverse primer KY34 (5'-RTA YTT NGT NCG NCC RTC NCC YTC-3') (SEQ ID NO. 2) is based on consensus amino acid sequence (EGDGRTKY; SEQ ID NO: 25) from B. napus AHAS1 and AHAS3 only in order to amplify the very end of the ORFs of the AHAS genes.

Leaf Genomic DNA was isolated using DNEASY 96 Plant Kit according to the manufacturer's instructions (QIAGEN). For PCR, 100 ng of leaf genomic DNA was used in a total volume of 50 µl, containing 5 µl of 10×Taq DNA polymerase buffer, 1.5 mM $MgCl_2$ and 2 units of Taq DNA polymerase (InvitroGen), 0.25 µM each of primers KY33 and KY34, and 50 µM of each dNTP. The amplification was done with initial incubation at 94° C. for 5 min followed by 35 cycles of 40 sec at 94° C., min at 56° C. and 2 min at 72° C., then the PCR mixture was incubated at 72° C. for 10 min. The PCR products (~1.6 kb) were purified and cloned into a cloning vector pDrive (Qiagen). The inserts were completely sequenced by a PRISM DYEDEOXY Teminator Cycle Sequencing Kit using a 377 DNA Sequencer. Sequence analysis was performed with the Lasergene DNA software kit (DNASTAR Inc.). For both B. juncea and B. nigra AHAS genes, multiple clones obtained from at least two independent PCR amplifications were sequenced to confirm that there were no PCR-related cloning artifacts.

Sequence analysis of the inserts confirmed that two AHAS genes were isolated from B. juncea, designated BjAHAS-a (SEQ ID NO. 8; SEQ ID NO. 11) and BjAHAS-b (SEQ ID NO. 9; SEQ ID NO. 12), respectively, based on their genome origins. Only one AHAS gene was isolated from B. nigra, designated BngrAHAS (SEQ ID NO. 10; SEQ ID NO. 13). Because of the degeneracy of the reverse primer KY34 the accuracy of the 3' end sequences of the isolated AHAS genes were confirmed by a 3' RACE technique. For this purpose, reverse primer Uni-TI 7 (5'-GTAAAACGACGGCCAGTCGATTTTTTTTT TTTTTTT-3') ((SEQ ID NO. 4) was used for the first strand cDNA synthesis using total RNA. Then, forward primer KY35 (5'-TGGTGGAAGCTTGAACTCG-3') (SEQ ID NO. 3) and reverse primer Uni (5'-GTAAAACGACG-GCCAGTCGA-3') (SEQ ID NO. 5) were used for PCR. Primer Uni-T17 and primer Uni are artificial primers. Primer KY35 is a gene specific primer designed according to the identical sequences of the three Brassica AHAS genes, BjAHAS-a, BjAHAS-b and BngrAHAS. The PCR products were cloned and sequenced.

The originally isolated DNA sequence lacked ~300 bp from the 5' end of the ORF, which encodes mostly the putative transit peptides (Rutledge et al., Mol. Gen. Genet. 229: 3140, 1991). To isolate the missing 5' end of the AHAS genes, PCRs were performed with leaf genomic DNA isolated from both B. juncea and B. nigra using the primer KY33A (forward) and primer KY36 (reverse). Primer KY33A (5'-CACGTTCACAAA CTCATTCATCA-3') (SEQ ID NO. 6) was designed corresponding to the identical sequences at the un-translated regions (5'-UTR) of both AHAS1 and AHAS3 cDNAs of B. napus. Primer KY36 (5'-ACTCGAGTTCAAGCTTCCACCA-3') (SEQ ID NO. 7) was designed corresponding to the identical sequences at the ~560 bp form the 5' end of the original partial sequences of BjAHAS-a, BjAHAS-b and BngrAHAS. Thus the ~860 bp new amplified fragments should include the start codon ATG at the 5' end of BjAHAS-a, BjAHAS-b and BngrAHAS. The overlapping sequences at the 3' end should provide information to confirm genome origins of each gene sequence.

Sequence analysis indicated that the BjAHAS-a gene contains an ORF of 1959 bp, which is predicted to encode a polypeptide of 652 aa; that the BjAHAS-b gene contains an ORF of 1968 bp, which is predicted to encode a polypeptide of 655 aa; and that the BngrAHAS gene contains an ORF of 1968 bp, which is predicted to encode a polypeptide of 655 aa. DNA and protein sequence comparisons indicated that BjAHAS-a shares 99.6% nucleotide sequence identity with the *B. napus* AHAS3 gene (A genome), and that the encoded protein BjAHAS-a shares 100% amino acid identity with the *B. napus* AHAS3. Whereas the BjAHAS-b share 99.9% nucleotide sequence identity with the BngrAHAS and that encoded protein BjAHAS-b shares 100% amino acid identity with the BngrAHAS (B genome). However, BjAHAS-b shares only 93.8% nucleotide sequence identity with the *B. napus* AHAS3 gene. The BjAHAS-a and BjAHAS-b share 93.8% nucleotide sequence identity and 99.1% amino acid identity of the encoded proteins with each other. These data clearly indicate that the two *B. juncea* AHAS genes, BjAHAS-a and BjAHAS-b, belong to A genome and B genome of *B. juncea*, respectively (FIG. 1). Comparison with the *B. napus* AHAS1 gene (C genome) indicated that the BjAHAS-a shares 97.9% nucleotide sequence identity with the *B. napus* AHAS1 gene; and that BjAHAS-b share 94.1% nucleotide sequence identity with the *B. napus* AHAS1 gene. The data indicated that the AHAS genes from the B genome (BjAHAS-b and BngrAHAS) are genetically more distant from the AHAS genes from the A genome (BjAHAS-a and the *B. napus* AHAS3) or AHAS gene from the C genome (*B. napus* AHAS1). All *Brassica* AHAS genes have relatively greater genetic diversity from the *Arabidopsis* AHAS gene (GenBank Accession No. 1501386 B).

Example 3

Expression of the BjAHAS-a and BjAHAS-b Genes in Leaves Tissues

It is known that in *B. napus* the AHAS1 and AHAS3 are expressed in all somatic tissues but AHAS2 is expressed only in mature ovules and extra-embryonic tissues of immature seeds (Ouellet et al., Plant J. 2:321-330, 1992). To make sure that the BjAHAS-a and BjAHAS-b genes are expressed in somatic tissues including leaves, gene expression was determined in *B. juncea* leaves. For this purpose, reverse transcription-PCR (RT-PCR) was performed to measure gene expression using total RNA that was isolated from leaves with a method using TRIZOL reagent according to the manufacture's protocol (Invitrogen). One microgram of total RNA was used for cDNA synthesis, which was carried out at 42° C. for 1 hr in a total volume of 20 ul using KY34 (SEQ ID NO. 2) as the reverse primer and the SuperScript™ II as the reverse transcriptase according to the manufacture's protocol (Invitrogen). After heat denaturation at 70° C. for 10 min. the RT mixture was put on ice and 2 ul of this mixture was used in PCR. PCR conditions were the same as described above using KY33 (SEQ ID NO. 1) and KY34 (SEQ ID NO. 2) as primers. Products of RT-PCR were the same size as the products of direct genomic PCR after electrophoresis on 1% agarose gel (~1.6 kb). Negative controls (minus the SUPERSCRIPT II reverse transcriptase) failed to amplify any product which confirmed that the products of RT-PCR were indeed from RNA.

Following gel electrophoresis, the RT-PCR products were purified and cloned into pDrive cloning vector (Qiagen) and the inserts were sequenced as described above. Sequence analysis of the inserts indicated that two unique sequences that are identical to BjAHAS-a and BjAHAS-b were isolated. The gene expression by RT-PCR confirmed that both BjAHAS-a and BjAHAS-b are expressed in leaf tissues. Therefore, BjAHAS-a and BjAHAS-b are indeed the two gene family members that play the essential AHAS housekeeping functions in *B. juncea* as do the AHAS1 and AHAS3 in *B. napus* (Ouellet et al., Plant J. 2:321-330, 1992).

Example 4

Mutant Allele of the BjAHAS-b Gene Locus from Line J04E-0044

*B. juncea* line J04E-0044 was created through EMS mutagenesis as described in Example 1. This line survived the imidazolinone herbicide spray, indicating herbicide resistant AHAS activities in this line. Further, AHAS enzyme assays in the presence of imidazolinone inhibitors confirmed that indeed there is herbicide resistant AHAS activity, which most likely is caused by mutations of either BjAHAS-a or BjAHAS-b or both.

To discover the mutation(s) of AHAS genes in mutant line J04E-0044, both BjAHAS-a and BjAHAS-b were cloned and sequenced using the method described in Example 2. At least two independent PCR amplifications were cloned and multiple plasmids of each PCR amplification were sequenced to confirm that there were no PCR-related cloning artifacts. Sequence analysis indicated that for BjAHAS-a, no nucleotide change from the BjAHAS-a of the wild type *B. juncea* Arid (SEQ ID NO. 8) was found. Therefore, the primary peptide sequences of BjAHAS-a from mutant line J04E-0044 is identical to that of wild type cultivar Arid.

For the BjAHAS-b gene from mutant line J04E-0044 a single basepair change (G to A transition) was found. This single nucleotide mutation changes the codon of AGT to AAT near the 3' end of the BjAHAS-b gene (SEQ ID NO. 9 and SEQ ID NO. 14), which predicts a Ser to Asn substitution at the C terminal of the predicted BjAHAS-b protein (SEQ ID NO. 12 and SEQ ID NO. 15). The amino acid residue "Ser" of the wild type BjAHAS-b protein resides in a short conserved peptide sequence "Ile Pro Ser Gly Gly" (SEQ ID NO. 20). In fact, this short peptide sequence "Ile Pro Ser Gly Gly" (SEQ ID NO: 20) is conserved in all known plant AHAS genes including BjAHAS-a (SEQ ID NO. 11), BjAHAS-b (SEQ ID NO12), and BngrAHAS (SEQ ID NO. 13), and *Arabidopsis* AHAS (GenBank Accession No. 1501386 B). The mutant allele of BjAHAS-b gene locus is hereafter named as BjAHAS-bR for its resistance to imidazolinones. It was reported previously by Hattori et al., (Mol Gen Genet 232: 167-173, 1992) that the *Arabidopsis* AHAS mutant imr1 also contains a G to A transition mutation that changes the codon AGT to AAT, which predicts a Ser to Asn substitution in the conserved peptide sequence "Ile Pro Ser Gly Gly" (SEQ ID NO: 22). Therefore, the *B. juncea* AHAS mutant line J04E-0044 (BjAHAS-bR) shares the same type of mutation with the *Arabidopsis* AHAS mutant imr1 (FIG. 2).

Two lines of evidence support the concept that BjAHAS-b and BjAHAS-bR are allelic to each other (same gene locus). First, a DNA sequence comparison shows that they are identical except the one single basepair change (G to A transition). Second, all B genome AHAS genes from line J04E-0044 are BjAHAS-bR alleles, suggesting that BjAHAS-b and BjAHAS-bR are at the same locus and that line J04E-0044 is homozygous at least in gene locus BjAHAS-b.

As demonstrated in Example 2, BjAHAS-b belongs to the B genome of *B. juncea*. Therefore, the mutant allele BjAHAS-bR is localised in the B genome.

Using techniques well known in the art, additional mutants having homology of 95%, 96%, 97%, 98% and 99% to BjAHAS-b are produced by skilled molecular biologists.

Example 5

Development of Gene Locus/Allele-Specific PCR Markers

The BjAHAS-bR allele disclosed in the present invention provides a valuable genetic resource for plant breeding. Specifically, it is valuable for breeding herbicide resistant *Brassica* species, including *B. juncea, B. nigra* and *B. carinata*. Development of a marker distinguishing the single basepair mutation may provide a simple way for segregation and selection analysis of genetic crosses involving plants having the BjAHAS-bR allele. In such crosses, the other parent plant may have the mutant allele, BjAHAS-bR, or may have the wild type allele, BjAHAS-b. In such crosses, the other parent plant may have other herbicide resistance AHAS gene mutations that are not allelic to gene locus BjAHAS-b/BjAHAS-bR.

As described in Example 4, the herbicide resistance allele BjAHAS-bR is different from the wild type allele BjAHAS-b by a single basepair change. It is possible to design allele-specific PCR primers using a 3' mismatch. For example, allele specific PCR primers were used to amplify different alleles of the FAD2 genes in *B. rapa* and *B. napus* (Tanhuanpää et al., Molecular Breeding 4: 543-550, 1998; U.S. Pat. No. 6,342,658, to DeBonte et al., issued on Jan. 29, 2002). Also available are many other methods for detecting single nucleotide polymorphisms (SNPs), which could be used for this kind of marker development. These methods include, but are not limited to, TaqMan assay and Molecular Beacon assay (Täpp et al., BioTechniques 28: 732-738), Invader Assays (Mein et al., Genome Research 10: 330-343, 2000) and single strand conformational polymorphism (SSCP) (Orita et al., Proc. Natl. Acad. Sci. U.S.A. 86:2766-2770, 1989).

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *Brassica* plants, using transformation methods as described below to incorporate transgenes into the genetic material of the *Brassica* plant(s).

Expression Vectors for *Brassica* Transformation: Marker Genes—Expression vectors include at least one genetic marker, operably linked to a regulatory element (a promoter, for example) that allows transformed cells containing the marker to be either recovered by negative selection, i.e., Inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, which, when under the control of plant regulatory signals confers resistance to kanamycin (Fraley et al., Proc. Natl. Acad. Sci. U.S.A., 80:4803, 1983). Another commonly used selectable marker gene is the hygromycin phosphotransferase gene which confers resistance to the antibiotic hygromycin (Vanden Elzen et al., Plant Mol. Biol., 5:299, 1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., Plant Physiol. 86:1216, 1988; Jones et al., Mol. Gen. Genet., 210:86, 1987; Svab et al., Plant Mol. Biol. 14:197, 1990; Hille et al., Plant Mol. Biol. 7:171, 1986). Other selectable marker genes confer resistance to herbicides such as glyphosate, glufosinate or bromoxynil (Comai et al., Nature 317:741-744, 1985; Gordon-Kamm et al., Plant Cell 2:603-618, 1990; Stalker et al., Science 242:419-423, 1988).

Other selectable marker genes for plant transformation not of bacterial origin include, for example, mouse dihydrofolate reductase, plant 5-enol-pyruvyl-shikimate-3-phosphate synthase and plant acetolactate synthase (Eichholtz et al., Somatic Cell Mol. Genet. 13:67, 1987; Shah et al., Science 233:478, 1986; Charest et al., Plant Cell Rep. 8:643, 1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387, 1987; Teeri et al., EMBO J. 8:343, 1989; Koncz et al., Proc. Natl. Acad. Sci U.S.A. 84:131, 1987; DeBlock et al., EMBO J. 3:1681, 1984).

In vivo methods for visualizing GUS activity that do not require destruction of plant tissue are available (Molecular Probes publication 2908, IMAGENE GREEN, p. 1-4, 1993; and Naleway et al., J. Cell Biol. 115:151a, 1991). However, these in vivo methods for visualizing GUS activity have not proven useful for recovery of transformed cells because of low sensitivity, high fluorescent backgrounds and limitations associated with the use of luciferase genes as selectable markers. A gene encoding Green Fluorescent Protein (GFP) has been utilized as a marker for gene expression in prokaryotic and eukaryotic cells (Chalfie et al., Science 263: 802, 1994). GFP and mutants of GFP may be used as selectable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in *Brassica*. Optionally, the inducible promoter is operably linked to a nucleotide sequence encoding a signal sequence which is operably linked to a gene for expression in *Brassica*. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571, 1993); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. U.S.A. 88:0421 (1991)).

B. Constitutive Promoters—A constitutive promoter is operably linked to a gene for expression in *Brassica* or the constitutive promoter is operably linked to a nucleotide sequence encoding a signal sequence which is operably linked to a gene for expression in *Brassica*.

Many different constitutive promoters can be utilized in the instant invention. Exemplary constitutive promoters include, but are not limited to, the promoters from plant viruses such as the 35S promoter from CaMV (Odell et al., Nature 313:810-812, 1985) and the promoters from such genes as rice actin (McElroy et al., Plant Cell 2:163-171, 1990); ubiquitin (Christensen et al., Plant Mol. Biol. 12:619-632, 1989; Christensen et al., Plant Mol. Biol. 18:675-689 (1992); pEMU (Last et al., Theor. Appl. Genet. 81:581-588, 1991); MAS (Velten et al., EMBO J. 3:2723-2730, 1984); maize H3 histone (Lepetit et al., Mol. Gen. Genetics 231: 276-285, 1992; Atanassova et al., Plant Journal 2 (3): 291-300, 1992).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in *Brassica*. Optionally, the tissue-specific promoter is operably linked to a nucleotide sequence encoding a signal sequence which is operably linked to a gene for expression in *Brassica*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Mural et al., Science 23:4768482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Fontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a *Brassica* plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., Plant Mol. Biol. 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci 89:43 (1993), of heterologous expression of a cecropin B, a lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an Immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonans. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvyl-shikimate-3-phosphate synthase (EPSPS) and aroA genes, respectively) and other phosphono compounds such as glufosinate (phosphinothricin acetyl transferase (PAT)) and Streptomyces hygroscopicus PAT, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przbila et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an Aspergillus niger phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of Streptococcus mutants fructosyltransferase gene), Steinmetz et al., Mol. Gen. Genet. 20:220 (1985) (nucleotide sequence of Bacillus subtilis levansucrase gene), Pen et al., Bio/Technology 10:292 (1992) (production of transgenic plants that express Bacillus lichenifonnis α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., Plant Physiol. 102:1045 (1993) (maize endosperm starch branching enzyme II).

Methods for Brassica Transformation—Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. Agrobacterium-mediated Transformation—One method for introducing an expression vector into plants is based on the natural transformation system of Agrobacterium. See, for example, Horsch et al., Science 227:1229 (1985). A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. See, for example, Kado, C. I., Crit. Rev. Plant Sci. 10:1 (1991). Descriptions of Agrobacterium vector systems and methods for Agrobacterium-mediated gene transfer are provided by Gruber et al., supra, Miki et al., supra, and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of *Brassica* target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular *Brassica* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of *Brassica*—Further production of the *B. juncea* cultivar J04E-0044 can occur by self-pollination or by tissue culture and regeneration. Tissue culture of various tissues of *Brassica* and regeneration of plants therefrom is known. For example, the propagation of a *Brassica* cultivar by tissue culture is described in any of the following, but not limited to any of the following: Chuong et al., "A Simple Culture Method for *Brassica* Hypocotyl Protoplasts", Plant Cell Reports 4:46 (1985); Barsby, T. L., et al., "A Rapid and Efficient Alternative Procedure for the Regeneration of Plants from Hypocotyl Protoplasts of *Brassica napus*", Plant Cell Reports, (Spring, 1996); Kartha, K., et al., "In vitro Plant Formation from Stem Explants of Rape", Physiol. Plant, 31:217-220 (1974); Narasimhulu, S., et al., "Species Specific Shoot Regeneration Response of Cotyledonary Explants of *Brassicas*", Plant Cell Reports, (Spring 1988); Swanson, E., "Microspore Culture in *Brassica*", Methods in Molecular Biology, Vol. 6, Chapter 17, p. 159 (1990).

Thus, another aspect of this invention is to provide cells which upon growth and differentiation produce *Brassica* plants having the physiological and morphological characteristics of *B. juncea* variety J04E-0044.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques, the disclosures of which are incorporated herein by reference.

Single Gene Conversion—When the term "*Brassica* plant" is used in the context of the present invention, this also includes any single gene conversions of that group. The term "single gene converted plant" as used herein refers to those *Brassica* plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental *Brassica* plant which contributes the gene for the desired characteristic is termed the "nonrecurrent" or "donor parent". This terminology refers to the fact that the nonrecurrent parent is used one time in the backcross protocol and therefore does not recur. The parental *Brassica* plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Brassica* plant is obtained wherein essentially all of the desired morphological and physiological characteristics of the recurrent parent are recovered in the converted plant, in addition to the single transferred gene from the nonrecurrent parent as determined at the 5% significance level when grown under the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

This invention also is directed to methods for producing a *Brassica* plant by crossing a first parent *Brassica* plant with a second parent *Brassica* plant wherein the first or second parent *Brassica* plant is a *Brassica* plant of the variety J04E-0044. Further, both first and second parent *Brassica* plants can come from the *Brassica* variety J04E-0044. Thus, any such methods using the *Brassica* variety J04E-0044 are part of this invention: selfing, backcrosses, hybrid production, crosses to populations, and the like. All plants produced using *Brassica* variety J04E-0044 as a parent are within the scope of this invention, including those developed from varieties derived from *Brassica* variety J04E-0044. Advantageously, the *Brassica* variety could be used in crosses with other, different, *Brassica* plants to produce first generation ($F_1$) *Brassica* hybrid seeds and plants with superior characteristics. The variety of the invention can also be used for transformation where exogenous genes are introduced and expressed by the variety of the invention. Genetic variants created either through traditional breeding methods using variety J04E-0044 or through transformation of J04E-0044 by any of a number of protocols known to those of skill in the art are intended to be within the scope of this invention.

BIBLIOGRAPHY

Agnihotri, A., Kaushik, N., Singh, N. K., Raney, J. P. and Downey, R. K. 1995. Selection for better agrononical and nutritional characteristics in Indian rapeseed-mustard. Proc. 9th Int. Rapeseed Cong., Cambridge, U.K. Vol. 2:425-427.

Daun, J. K. and McGregor, D. I. 1991. Glucosinolates in seeds and residues, In: Analysis of Oilseeds, Fats and Fatty foods. J. B. Rossell and J. L. R. Pritchard, eds. Elsevier Applied Science, London, pp. 185-226.

Downey, R. K. and Rakow, G. F. W. 1987. Rapeseed and mustard. In: Principles of cultivar development. W. R. Fehr, ed. Macmillian, N.Y. Pp. 437-486.

Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.

Love, H. K., Rakow, G., Raney, J. P. and Downey, R. K. 1990. Development of low glucosinolate mustard. Can. J. Plant Sci. 70:419-424.

Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. Vol. 1:164-169.

Potts et al., 1999. Canola-quality *Brassica juncea*, a new oilseed crop for the Canadian prairies. The proceedings of 10th International Rapeseed Congress in Sep. 26-29, 1999; Canberra, Australia; CD-ROM.

Potts and Males. 1999. Inheritance of fatty acid composition in *Brassica juncea*. The proceedings of 10th International Rapeseed Congress in Sep. 26-29, 1999; Canberra, Australia; CD-ROM.

Rakow, G. 1991. Canola quality mustard. Proc. Special Cropportunities I: A conference organized by the Crop Development Centre and the Extension Division, University of Saskatchewan, Saskatoon, Canada pp. 55-59.

Rakow, G., Raney, J. P. and Males, D. 1995. Field performance of canola quality *B. juncea*. Proc. 9.sup.th Int. Rapeseed Congress, Cambridge, U.K. Vol. 2:428-430.

Raney, P., Rakow, G. and Olson, T. 1995. Development of zero erucic, low linolenic *B. juncea* utilizing interspecific crossing. Proc. 9.sup.th Int. Rapeseed Congress, Cambridge, U.K. Vol. 2:413-415.

Stotjesdijk et al., 1999. Genetic manipulation for altered oil quality in *Brassica*. The proceedings of 10th International Rapeseed Congress in Sep. 26-29, 1999; Canberra, Australia; CD-ROM.

Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7:83-87.

Swanson, E. B., Herrgesell, M. J., Amoldo, M., Sippell, D. W. and Wong, R. S. C. 1989. Microspore mutagenesis and selection: canola plants with field tolerance to the imidazolinones. Theor. Appl. Genet. 78:525530.

Thiagarajah, M. R. and Stringham, G. R. 1993. A comparison of genetic segregation in traditional and microspore-derived populations of *B. juncea* L. Czem and Coss. Plant Breeding 111:330-334.

U, N. 1935. Genome analysis in *Brassica* with special reference to the experimental formation of *B. napus* and peculiar mode of fertilization. Jap. J. Bot. 7:389-452).

Woods, D. L., Capeara, J. J. and Downey, R. K. 1991. The potential of mustard (*B. juncea* (L.) Coss) as an edible oil crop on the Canadian Prairies. Can. J. Plant Sci. 71:195-198.

What is claimed is:

1. A *Brassica juncea* plant obtained by a process comprising crossing a plant of line J04E-0044, a representative sample of seed of the line having been deposited under ATCC Accession No. PTA-6324, with another *Brassica* variety,
   wherein the plant comprises a B-genome having a *Brassica juncea* acetohydroxyacid synthase (AHAS) nucleic acid at the AHAS-b locus thereof, the nucleic acid encoding an herbicide resistant AHAS polypeptide comprising amino acid residues 114 to 655 of SEQ ID NO:15, said plant exhibiting increased tolerance to an AHAS-inhibiting herbicide as compared to that of a corresponding wild-type plant.

2. The *Brassica juncea* plant of claim 1, wherein the AHAS-inhibiting herbicide is an imidazolinone herbicide.

3. A method of producing *Brassica juncea* plant lines wherein the method comprises:
   a) making a cross involving a first parent and a second parent plant, wherein the first plant is a plant of line J04E-0044, a representative sample of seed of the line having been deposited under ATCC Accession No. PTA-6324 and comprises a B-genome having a *Brassica juncea* acetohydroxyacid synthase (AHAS) nucleic acid at the AHAS-b locus thereof, the nucleic acid encoding an herbicide resistant AHAS a polypeptide comprising amino acid residues 114 to 655 of SEQ ID NO:15;
   b) obtaining seeds from the cross of step (a);
   c) growing fertile plants from such seeds;
   d) identifying progeny plants that are herbicide resistant and that comprise a polynucleotide encoding a polypeptide comprising amino acid residues 114 to 655 of SEQ ID NO:15; and
   e) obtaining progeny seeds from plants identified in step (d), wherein the *Brassica juncea* plant lines are commercial *Brassica juncea* plant lines.

4. The method of claim 3, wherein said herbicide resistant plant is resistant to an imidazolinone herbicide.

5. The plant of claim 1, wherein the AHAS nucleic acid comprises nucleotides 396 to 2024 of SEQ ID NO:14.

6. A seed of the *Brassica juncea* plant of claim 1.

7. The seed of claim 6, wherein the seed is untreated.

8. The seed of claim 6, wherein the seed is sprayed with imidazolinone herbicide.

9. A method to control weeds in a *Brassica* crop comprising applying an herbicide to weeds in said crop, wherein the *Brassica* crop comprises the plant of claim 1.

10. The method of claim 9, wherein the herbicide comprises an imidazolinone herbicide.

11. The method of claim 9, wherein the herbicide comprises imazamox.

12. The method of claim 9, wherein said method comprises applying the herbicide to a seed from which the plant is grown.

13. The plant of claim 1, wherein the AHAS nucleic acid sequence has been obtained by ethyl methyl sulfonate (EMS) mutagenesis.

14. The plant of claim 1, wherein the AHAS nucleic acid sequence is non-recombinant.

15. The plant of claim 1, wherein the plant is a commercial *Brassica juncea* plant.

16. A plant part or plant cell of the plant of claim 1 comprising the AHAS nucleic acid.

17. The method of claim 3, wherein the AHAS nucleic acid sequence has been obtained by ethyl methyl sulfonate (EMS) mutagenesis.

18. The method of claim 3, wherein the AHAS nucleic acid sequence is non-recombinant.

* * * * *